US012599368B2

(12) United States Patent
Matsumoto

(10) Patent No.: US 12,599,368 B2
(45) Date of Patent: Apr. 14, 2026

(54) INFORMATION PROCESSING APPARATUS, INFORMATION PROCESSING METHOD, AND PROGRAM

(71) Applicant: FUJIFILM Corporation, Tokyo (JP)

(72) Inventor: Tsuyoshi Matsumoto, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 244 days.

(21) Appl. No.: 18/310,032

(22) Filed: May 1, 2023

(65) Prior Publication Data

US 2023/0263505 A1     Aug. 24, 2023

Related U.S. Application Data

(63) Continuation of application No. PCT/JP2021/034782, filed on Sep. 22, 2021.

(30) Foreign Application Priority Data

Nov. 19, 2020     (JP) ................................. 2020-192752

(51) Int. Cl.
  *A61B 8/00*     (2006.01)
  *A61B 8/08*     (2006.01)
(52) U.S. Cl.
  CPC .......... *A61B 8/5223* (2013.01); *A61B 8/0891* (2013.01); *A61B 8/461* (2013.01); *A61B 8/469* (2013.01)
(58) Field of Classification Search
  CPC ..... A61B 8/5223; A61B 8/0891; A61B 8/461; A61B 8/469; A61B 8/4427; A61B 8/085;
  (Continued)

(56) References Cited

U.S. PATENT DOCUMENTS 6,245,018 B1 *  6/2001  Lee ..................... G01S 7/52071
                                                  600/454
2005/0075566 A1   4/2005  Satoh
                 (Continued)

FOREIGN PATENT DOCUMENTS

CN     102078202 A     6/2011
CN     104873223 A     9/2015
                 (Continued)

OTHER PUBLICATIONS

International Search Report issued in PCT/JP2021/034782; mailed Dec. 14, 2021.
                 (Continued)

*Primary Examiner* — Peter Luong
(74) *Attorney, Agent, or Firm* — Studebaker Brackett PLLC

(57)          ABSTRACT

The information processing apparatus performs processing of causing a display device (21) to display an ultrasound image (U), which is generated by transmitting ultrasound beams (UB) from a transducer array (13) toward the inside of a living body (30) and receiving ultrasound echoes generated in the living body (30). The information processing apparatus includes: a blood vessel aggregate detection unit (72) that detects, from the ultrasound image (U), a blood vessel aggregate region (Ra) including a blood vessel aggregate in which three or more blood vessels (B) are aggregated; and a highlight display unit (54) that highlights and displays the blood vessel aggregate region (Ra) in the ultrasound image (U).

12 Claims, 19 Drawing Sheets

(58) Field of Classification Search

CPC ......... A61B 8/463; A61B 8/5207; A61B 8/06; A61B 8/0858; G06T 7/0012; G06T 2207/10132; G06T 2207/20084; G06T 2207/30101

See application file for complete search history.

(56) References Cited

U.S. PATENT DOCUMENTS

| | | | | |
|---|---|---|---|---|
| 2011/0166451 | A1 * | 7/2011 | Blaivas | A61B 8/467 |
| | | | | 600/439 |
| 2013/0197367 | A1 * | 8/2013 | Smok | A61B 8/085 |
| | | | | 600/454 |
| 2015/0245820 | A1 | 9/2015 | Tamada | |
| 2016/0324423 | A1 | 11/2016 | Irisawa et al. | |
| 2018/0014810 | A1 | 1/2018 | Chen et al. | |
| 2021/0137492 | A1 | 5/2021 | Imai | |

FOREIGN PATENT DOCUMENTS

| | | | |
|---|---|---|---|
| CN | 105916446 A | | 8/2016 |
| EP | 3 708 088 A1 | | 9/2020 |
| JP | 2001-187052 A | | 7/2001 |
| JP | 2005-111258 A | | 4/2005 |
| JP | 2008-284162 A | | 11/2008 |
| JP | 2014004149 A | * | 1/2014 |
| JP | 2017-524455 A | | 8/2017 |
| WO | WO-2020044769 A1 | * | 3/2020 ............... A61B 8/06 |
| WO | WO-2020044770 A1 | * | 3/2020 ............... A61B 8/08 |
| WO | 2020/087732 A1 | | 5/2020 |

OTHER PUBLICATIONS

International Preliminary Report On Patentability (Chapter I) and Written Opinion of the International Searching Authority issued in PCT/JP2021/034782; issued May 16, 2023.

The extended European search report issued by the European Patent Office on Oct. 24, 2023, which corresponds to European Patent Application No. 21894315.7-1126 and is related to U.S. Appl. No. 18/310,032.

Liangsheng, H. et al; "Study on Automatic Venipuncture Device and Control System"; Chinese Journal of Medical Instrumentation; Mar. 31, 2017; pp. 200-203; vol. 41, No. 3; China Academic Journal Electronic Publishing House; DOI:10.3969/j.issn.1671-7104.2017.03.012.

Gerard, M.; "3D Modeling of Hepatic Arteries and Visualization Through Fusion of Magnetic Resonance Imaging and Ultrasonic Imaging"; Thesis Presented for the Degree of Master of Applied Sciences (Biomedical Engineering); Dec. 31, 2016; total 24 pages; Polytechnique Montréal; URL: https://publications.polymtl.ca/2390/.

An Office Action; mailed by the China National Intellectual Property Administration of the People's Republic of China on Jun. 4, 2025, which corresponds to Chinese Patent Application No. 202180076543.X and is related to U.S. Appl. No. 18/310,032.

* cited by examiner

FIG. 1

ARTERY/VEIN DETERMINATION PROCESSING

CALCULATE FEATURE AMOUNTS OF EACH OF BLOOD VESSELS B
(FEATURE AMOUNTS: BLOOD VESSEL DIAMETER D, DISPLACEMENT
AMOUNT K, OR CIRCULARITY)

SCORE CALCULATION AND LABEL DETERMINATION

INFORMATION PROCESSING APPARATUS, INFORMATION PROCESSING METHOD, AND PROGRAM

CROSS-REFERENCE TO RELATED APPLICATION

This application is a continuation application of International Application No. PCT/JP2021/034782, filed Sep. 22, 2021, the disclosure of which is incorporated herein by reference in its entirety. Further, this application claims priority from Japanese Patent Application No. 2020-192752 filed on Nov. 19, 2020, the disclosure of which is incorporated herein by reference in its entirety.

BACKGROUND

1. Technical Field

A technique of the present disclosure relates to an information processing apparatus, an information processing method, and a program.

2. Description of the Related Art

In the related art, an ultrasound diagnostic apparatus has been known as an apparatus that obtains an image of the inside of a subject. In general, an ultrasound diagnostic apparatus includes an ultrasound probe provided with a transducer array in which a plurality of ultrasound transducers are arranged. The ultrasound probe transmits ultrasound beams from the transducer array toward the inside of the subject in a state of being in contact with a body surface of the subject, and receives ultrasound echoes from the subject by the transducer array. Thereby, an electric signal corresponding to the ultrasound echoes is acquired. Further, the ultrasound diagnostic apparatus generates an ultrasound image for the corresponding portion of the subject by processing the acquired electric signal.

By the way, a technique (so-called echo-guided puncture method) of inserting a so-called puncture needle into a blood vessel of a subject while observing the inside of the subject using an ultrasound diagnostic apparatus is known. In the echo-guided puncture method, an operator usually needs to recognize positions, shapes, and the like of blood vessels included in an ultrasound image by confirming the ultrasound image. However, in order to accurately recognize positions, shapes, and the like of blood vessels, a certain level of proficiency is required. For this reason, a technique of automatically detecting blood vessels included in an ultrasound image and presenting the detected blood vessels to an operator is proposed (refer to, for example, JP2017-524455A).

SUMMARY

In puncture, an operator needs to accurately determine whether a blood vessel is an artery or a vein based on the ultrasound image. Hereinafter, the determination will be referred to as artery/vein determination.

It is also considered to perform artery/vein determination of a blood vessel by information processing such as image analysis based on the ultrasound image. However, in a case where artery/vein determination is individually performed on the blood vessels, the determination is likely to be erroneous in a case where shapes and the like of arteries and veins are similar.

An object of the technique of the present disclosure is to provide an information processing apparatus, an information processing method, and a program capable of supporting artery/vein determination of a blood vessel.

According to an aspect of the present disclosure, there is provided an information processing apparatus that performs processing of causing a display device to display an ultrasound image, which is generated by transmitting ultrasound beams from a transducer array toward the inside of a living body and receiving ultrasound echoes generated in the living body, the apparatus including: a blood vessel aggregate detection unit that detects, from the ultrasound image, a blood vessel aggregate region including a blood vessel aggregate in which three or more blood vessels are aggregated; and a highlight display unit that highlights and displays the blood vessel aggregate region in the ultrasound image.

Preferably, the information processing apparatus further includes an artery/vein determination unit that determines whether each of the blood vessels included in the blood vessel aggregate region is an artery or a vein based on feature amounts of each blood vessel in the blood vessel aggregate region.

Preferably, the artery/vein determination unit performs determination based on at least one or more feature amounts of a blood vessel diameter, a displacement amount of the blood vessel from a center of the blood vessel aggregate region, or a circularity of the blood vessel.

Preferably, the information processing apparatus further includes a blood vessel single-body detection unit that detects a blood vessel single-body region including a blood vessel single-body from the ultrasound image and determines whether the blood vessel included in the detected blood vessel single-body region is an artery or a vein.

Preferably, the information processing apparatus further includes a correction unit that corrects a result of artery/vein determination by the blood vessel single-body detection unit based on a result of artery/vein determination by the artery/vein determination unit.

Preferably, the correction unit compares reliability of artery/vein determination by the blood vessel single-body detection unit with reliability of artery/vein determination by the artery/vein determination unit, and selects a determination result having higher reliability.

Preferably, the highlight display unit displays each of the blood vessels included in the blood vessel aggregate region such that an artery and a vein can be identified from each other based on a correction result by the correction unit.

Preferably, the highlight display unit displays, on the display device, reliability on the determination result selected by the correction unit.

Preferably, the highlight display unit displays, on the display device, a message urging an operator to pay attention in a case where the reliability on the determination result selected by the correction unit is lower than a certain value.

According to another aspect of the present disclosure, there is provided an information processing method for performing processing of causing a display device to display an ultrasound image, which is generated by transmitting ultrasound beams from a transducer array toward the inside of a living body and receiving ultrasound echoes generated in the living body, the method including: detecting, from the ultrasound image, a blood vessel aggregate region including a blood vessel aggregate in which three or more blood vessels are aggregated, and highlighting and displaying the detected blood vessel aggregate region in the ultrasound image.

According to another aspect of the present disclosure, there is provided a program causing a computer to execute a process of causing a display device to display an ultrasound image, which is generated by transmitting ultrasound beams from a transducer array toward the inside of a living body and receiving ultrasound echoes generated in the living body, the process including: processing of detecting, from the ultrasound image, a blood vessel aggregate region including a blood vessel aggregate in which three or more blood vessels are aggregated, and highlighting and displaying the detected blood vessel aggregate region in the ultrasound image.

According to the technique of the present disclosure, it is possible to provide an information processing apparatus, an information processing method, and a program capable of supporting artery/vein determination of a blood vessel.

BRIEF DESCRIPTION OF THE DRAWINGS

Exemplary embodiments according to the technique of the present disclosure will be described in detail based on the following figures, wherein:

FIG. 1 is an external view illustrating an example of a configuration of an ultrasound diagnostic apparatus according to a first embodiment,

DETAILED DESCRIPTION

Figure 2:
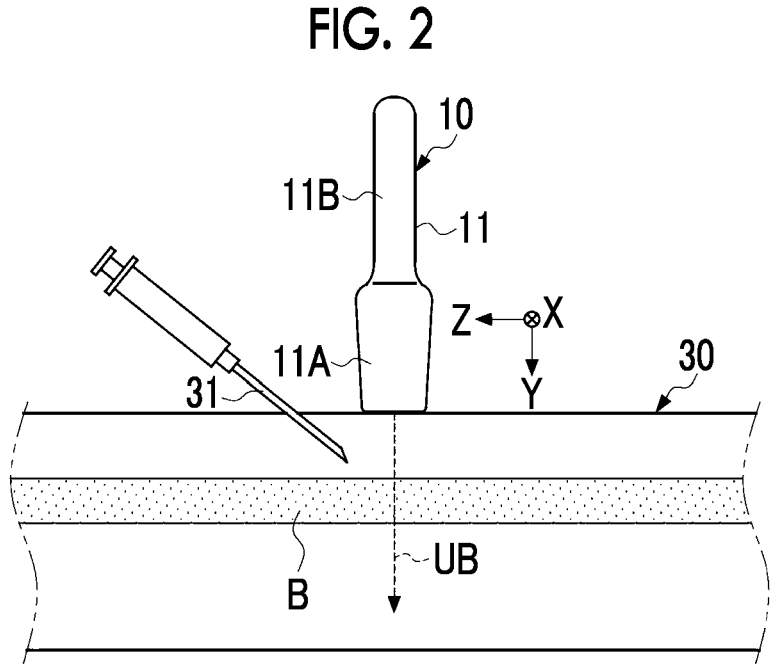
FIG. 2 is a diagram illustrating an example of an echo-guided puncture method.

Hereinafter, embodiments according to the technique of the present disclosure will be described with reference to the accompanying drawings. A description of components to be described below is based on a representative embodiment of the present disclosure. On the other hand, the technique of the present disclosure is not limited to such an embodiment.

First Embodiment

Figure 1:
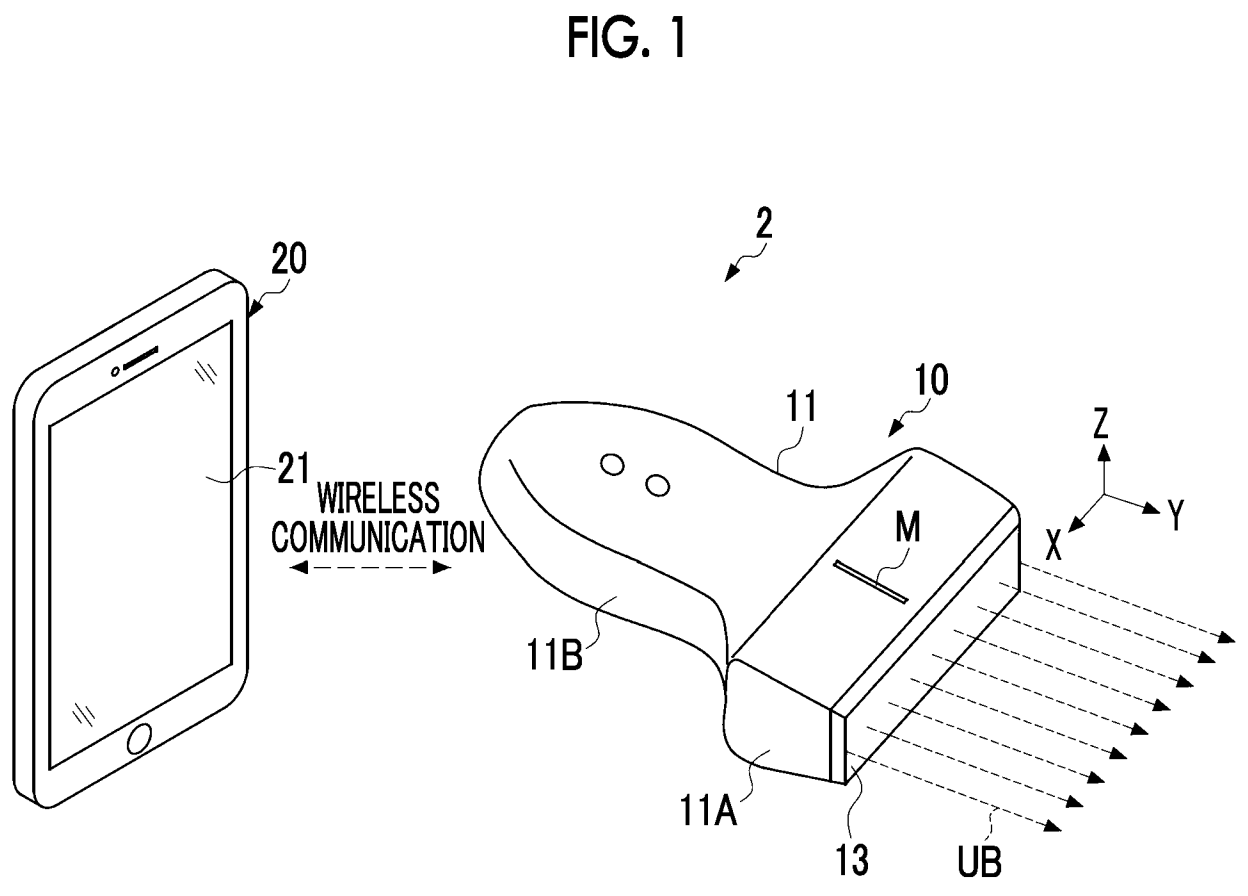

FIG. 1 illustrates an example of a configuration of an ultrasound diagnostic apparatus 2 according to the technique of the present disclosure. The ultrasound diagnostic apparatus 2 according to the present embodiment includes an ultrasound probe 10 and an apparatus main body 20. The ultrasound probe 10 is held by an operator and is brought into contact with a surface of a living body to be measured. The ultrasound probe 10 transmits and receives ultrasound beams to and from the inside of the living body.

The apparatus main body 20 is, for example, a smartphone, a tablet terminal, or the like. By installing a program such as application software in the apparatus main body 20, the apparatus main body 20 performs imaging of a signal or the like which is output from the ultrasound probe 10. The ultrasound probe 10 and the apparatus main body 20 perform wireless communication with each other by, for example, WiFi or Bluetooth (registered trademark). The apparatus main body 20 is not limited to a mobile terminal such as a smartphone or a tablet terminal, and may be a personal computer (PC) or the like. The apparatus main body 20 is an example of an "information processing apparatus" according to the technique of the present disclosure.

The ultrasound probe 10 includes a housing 11. The housing 11 is configured by an array housing part 11A and a grip portion 11B. The array housing part 11A houses a transducer array 13 (refer to FIG. 3). The grip portion 11B is connected to the array housing part 11A, and is gripped by the operator. Here, for the sake of explanation, a direction from the grip portion 11B toward the array housing part 11A is defined as a +Y direction, a width direction of the ultrasound probe 10 orthogonal to the Y direction is defined as an X direction, and a direction orthogonal to the X direction and the Y direction (that is, a thickness direction of the ultrasound probe 10) is defined as a Z direction.

An acoustic lens is disposed at an end portion of the array housing part 11A in the +Y direction. A so-called acoustic matching layer (not illustrated) is disposed on the transducer array 13, and the acoustic lens is disposed on the acoustic matching layer. A plurality of transducers included in the transducer array 13 are linearly arranged along the X direction. That is, the ultrasound probe 10 according to the present embodiment has a linear type, and linearly transmits ultrasound beams UBs. The ultrasound probe 10 may have a convex type in which the transducer array 13 is disposed in a convex curved shape. In this case, the ultrasound probe 10 radially transmits ultrasound beams UBs. Further, the ultrasound probe 10 may have a sector type.

In addition, a linear guide marker M extending along the Y direction is attached to an outer peripheral portion of the array housing part 11A. The guide marker M is used as a guide in a case where the operator brings the ultrasound probe 10 into contact with a living body.

The apparatus main body 20 includes a display device 21 for displaying an ultrasound image based on a signal transmitted from the ultrasound probe 10. The display device 21 is, for example, a display device such as an organic electroluminescence (organic EL) display or a liquid crystal display. A touch panel is incorporated in the display device 21. The operator can perform various operations on the apparatus main body 20 by using the touch panel.

FIG. 2 is a diagram illustrating an example of an echo-guided puncture method. As illustrated in FIG. 2, the ultrasound probe 10 is used in a case where the operator punctures a puncture needle 31 into a blood vessel B in a living body 30 while checking an ultrasound image displayed on the apparatus main body 20. The living body 30 is, for example, an arm of a person. In the ultrasound probe 10, for example, the ultrasound probe 10 is brought into contact with the surface of the living body 30 such that the width direction (that is, the X direction) of the ultrasound probe 10 crosses a traveling direction of the blood vessel B. This procedure is called a short-axis method (or crossing method). A cross section of the blood vessel B is displayed in the ultrasound image. The operator punctures, for example, a vein of one or more blood vessels B displayed in the ultrasound image.

The apparatus main body 20 supports puncturing by the operator by detecting a blood vessel from the ultrasound image, performing artery/vein determination of the blood vessel, and displays a result of the artery/vein determination in the ultrasound image displayed on the display device 21.

Figure 3:
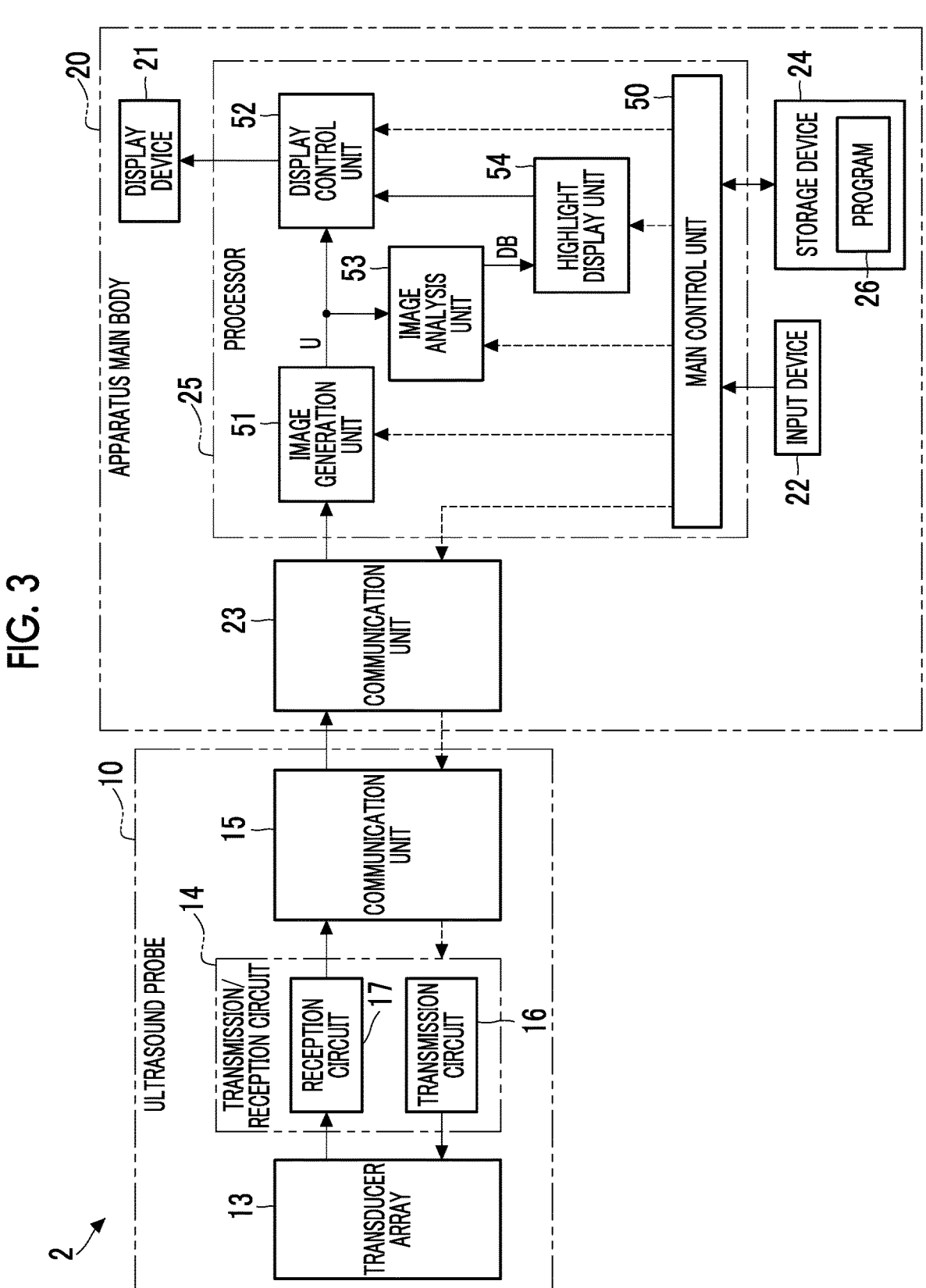
FIG. 3 is a block diagram illustrating an example of a configuration of the ultrasound diagnostic apparatus.

FIG. 3 illustrates an example of a configuration of the ultrasound diagnostic apparatus 2. The ultrasound probe 10 includes a transducer array 13, a transmission/reception circuit 14, and a communication unit 15. The transmission/reception circuit 14 includes a transmission circuit 16 and a reception circuit 17. The transmission circuit 16 and the reception circuit 17 are respectively connected to the transducer array 13. In addition, the transmission/reception circuit 14 transmits and receives signals to and from a processor 25 of the apparatus main body 20 via the communication unit 15.

The transducer array 13 includes a plurality of transducers (not illustrated) which are arranged in one-dimensional manner or two-dimensional manner. Each of these transducers transmits ultrasound beams UBs in accordance with a drive signal supplied from the transmission circuit 16 and receives ultrasound echoes from the living body 30. The transducer outputs a signal based on the received ultrasound echoes. The transducer is configured, for example, by forming electrodes at both ends of a piezoelectric body. The piezoelectric body includes a piezoelectric ceramic represented by lead zirconate titanate (PZT), a polymer piezoelectric element represented by poly vinylidene di fluoride (PVDF), a piezoelectric single crystal represented by lead magnesium niobate-lead titanate (PMN-PT), and the like.

The transmission circuit 16 includes, for example, a plurality of pulse generators. The transmission circuit 16 adjusts a delay amount of a drive signal based on a transmission delay pattern, which is selected according to a control signal transmitted from the processor 25 of the apparatus main body 20, and supplies the adjusted delay amount of the drive signal to the plurality of transducers included in the transducer array 13. The delay amount of the drive signal is adjusted by the transmission circuit 16 such that the ultrasound waves transmitted from the plurality of transducers form the ultrasound beams UBs. The drive signal is a pulsed or continuous voltage signal. In a case where the drive signal is applied, the transducers transmit pulsed or continuous ultrasound waves by expansion and contraction. By combining the ultrasound waves transmitted from the plurality of transducers, the ultrasound beams UBs as combined waves are formed.

In a case where the ultrasound beams UBs are transmitted into the living body 30, the ultrasound beams UBs are reflected by a part such as a blood vessel B in the living body 30. Thereby, ultrasound echoes are generated, and the ultrasound echoes propagate toward the transducer array 13. The ultrasound echoes which propagate toward the transducer array 13 in this way are received by the plurality of transducers included in the transducer array 13. In a case where the ultrasound echoes are received, the transducers generate electric signals by expansion and contraction. The electric signals generated by the transducers are output to the reception circuit 17.

Figure 4:
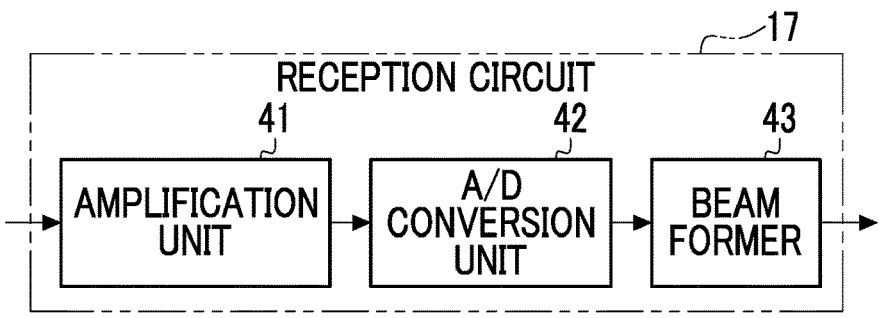
FIG. 4 is a block diagram illustrating an example of a configuration of a reception circuit.

The reception circuit 17 generates a sound wave signal by processing the electric signals output from the transducer array 13 according to a control signal transmitted from the processor 25 of the apparatus main body 20. As illustrated in FIG. 4 as an example, the reception circuit 17 is configured by connecting an amplification unit 41, an analog to digital (A/D) conversion unit 42, and a beam former 43 in series.

The amplification unit 41 amplifies the signal which is input from each of the plurality of transducers included in the transducer array 13, and transmits the amplified signal to the A/D conversion unit 42. The A/D conversion unit 42 converts the signal transmitted from the amplification unit 41 into digital reception data, and transmits the converted reception data to the beam former 43. The beam former 43 adds a delay to the reception data converted by the A/D conversion unit 42 according to a sound velocity or a sound velocity distribution which is set based on a reception delay pattern selected according to a control signal transmitted from the processor 25 of the apparatus main body 20. This addition processing is referred to as reception focus processing. By this reception focus processing, a sound wave signal, which is obtained by performing phasing addition on the reception data converted by the A/D conversion unit 42 and narrowing down a focus of the ultrasound echo, is acquired.

The apparatus main body 20 includes a display device 21, an input device 22, a communication unit 23, a storage device 24, and a processor 25. The input device 22 is, for example, a touch panel or the like incorporated in the display device 21. In a case where the apparatus main body 20 is a PC or the like, the input device 22 may be a keyboard, a mouse, a track ball, a touch pad, or the like. The communication unit 23 performs wireless communication with the communication unit 15 of the ultrasound probe 10.

The input device 22 and the storage device 24 are connected to the processor 25. The processor 25 and the storage device 24 are connected to each other such that information can be bidirectionally exchanged.

The storage device 24 is a device that stores a program 26 or the like for operating the ultrasound diagnostic apparatus 2, and is, for example, a flash memory, a hard disc drive (HDD), or a solid state drive (SSD). In a case where the apparatus main body 20 is a PC or the like, as the storage device 24, a recording medium such as a flexible disc (FD), a magneto-optical (MO) disc, a magnetic tape, a compact disc (CD), a digital versatile disc (DVD), a secure digital (SD) card, or a Universal Serial Bus (USB) memory, a server, or the like can be used.

The processor 25 is, for example, a central processing unit (CPU). The processor 25 performs processing based on the program 26 in cooperation with a random access memory (RAM) (not illustrated) or the like, and thus the apparatus main body 20 functions as a main control unit 50, an image generation unit 51, a display control unit 52, an image analysis unit 53, and a highlight display unit 54.

The processor 25 is not limited to the CPU. The processor 25 may be configured by a field programmable gate array (FPGA), a digital signal processor (DSP), an application specific integrated circuit (ASIC), a graphics processing unit (GPU), or another integrated circuit (IC), or may be configured by a combination thereof.

The main control unit 50 controls each unit of the ultrasound diagnostic apparatus 2 based on an input operation by the operator via the input device 22. The main control unit 50 transmits the above-described control signal to the ultrasound probe 10 via the communication unit 23. The sound wave signal generated by the reception circuit 17 is input from the ultrasound probe 10 to the processor 25 via the communication unit 23.

Figure 5:
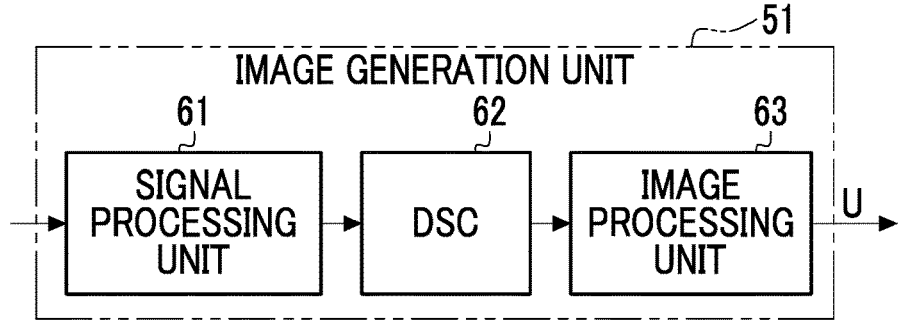
FIG. 5 is a block diagram illustrating an example of a configuration of an image generation unit.

The image generation unit 51 acquires the sound wave signal which is input from the ultrasound probe 10 under a control of the main control unit 50, and generates an ultrasound image U based on the acquired sound wave signal. As illustrated in FIG. 5 as an example, the image generation unit 51 is configured by connecting a signal processing unit 61, a digital scan converter (DSC) 62, and an image processing unit 63 in series.

The signal processing unit 61 performs, on the sound wave signal generated by the reception circuit 17, correction of attenuation due to a distance according to a depth of a reflection position of the ultrasound wave, and then performs envelope detection processing on the corrected sound wave signal. Thereby, a B-mode image signal, which is tomographic image information on a tissue in the subject, is generated.

The DSC 62 converts (so-called raster-converts) the B mode image signal generated by the signal processing unit 61 into an image signal conforming to a normal television signal scanning method. The image processing unit 63 performs various image processing such as gradation processing on the B mode image signal which is input from the DSC 62, and then outputs the B mode image signal to the display control unit 52 and the image analysis unit 53. In the following, the B mode image signal obtained by performing image processing by the image processing unit 63 is simply referred to as an ultrasound image U.

The transmission/reception circuit 14 of the ultrasound probe 10 and the image generation unit 51 are controlled by the main control unit 50 such that the ultrasound image U is periodically generated at a constant frame rate. The transmission/reception circuit 14 and the image generation unit 51 function as an image acquisition unit that acquires the ultrasound image U.

Under the control of the main control unit 50, the display control unit 52 performs predetermined processing on the ultrasound image U generated by the image generation unit 51, and causes the display device 21 to display the processed ultrasound image U.

Under the control of the main control unit 50, the image analysis unit 53 generates blood vessel detection information DB by performing image analysis on the ultrasound image U which is input from the image generation unit 51, and outputs the generated blood vessel detection information DB to the highlight display unit 54. The blood vessel detection information DB includes, for example, a detection result of a blood vessel region included in the ultrasound image U and a result of artery/vein determination of the detected blood vessel. In addition, the blood vessel region includes a "blood vessel single-body region" representing a region of a blood vessel single-body and a "blood vessel aggregate region" representing a region of a blood vessel aggregate in which three or more blood vessels are aggregated. The blood vessel aggregate is, for example, a composite body of an artery and an accompanying vein. The blood vessel aggregate is mainly present in an anatomically stable part.

The highlight display unit 54 controls the display control unit 52 based on the blood vessel detection information DB which is input from the image analysis unit 53 under the control of the main control unit 50. Thereby, the blood vessel single-body region and the blood vessel aggregate region are highlighted and displayed in the ultrasound image U displayed on the display device 21. In addition, the highlight display unit 54 displays the blood vessel single-body region based on the artery/vein determination result such that the blood vessel included in the blood vessel single-body region can be identified as an artery or a vein.

Figure 6:
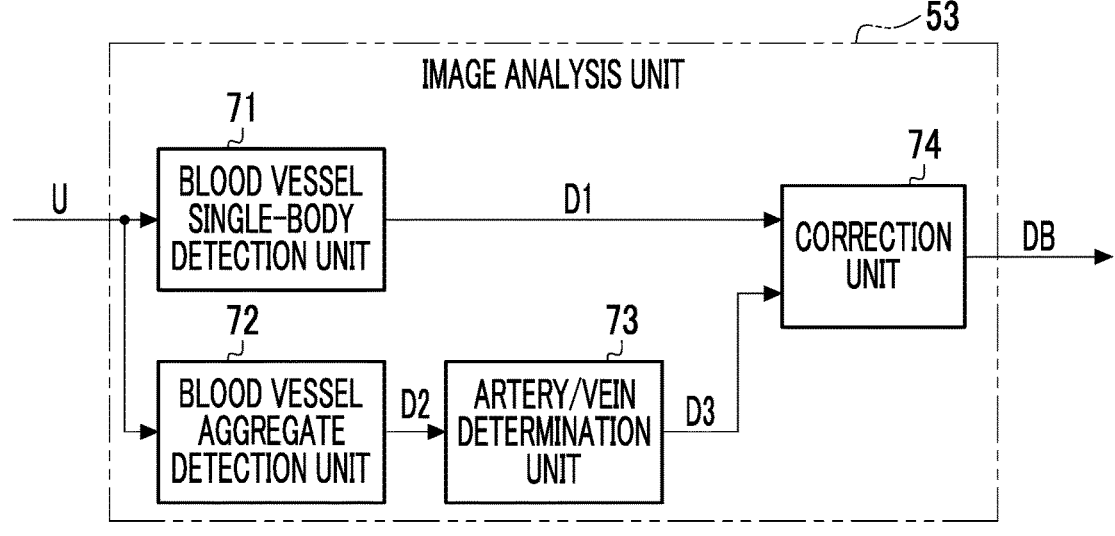
FIG. 6 is a block diagram illustrating an example of a configuration of an image analysis unit,

As illustrated in FIG. 6 as an example, the image analysis unit 53 includes a blood vessel single-body detection unit 71, a blood vessel aggregate detection unit 72, an artery/vein determination unit 73, and a correction unit 74. The ultrasound image U generated by the image generation unit 51 is input to the blood vessel single-body detection unit 71 and the blood vessel aggregate detection unit 72.

The blood vessel single-body detection unit 71 specifies a blood vessel single-body region by individually detecting each blood vessel included in the ultrasound image U, and performs artery/vein determination of the blood vessel included in the blood vessel single-body region. The blood vessel single-body detection unit 71 outputs information including a detection result of a blood vessel single-body region and an artery/vein determination result of the blood vessel single-body region to the correction unit 74, as blood vessel single-body detection information D1.

The blood vessel aggregate detection unit 72 detects a blood vessel aggregate region in which three or more blood vessels are aggregated based on the ultrasound image U, and outputs information representing the detected blood vessel aggregate region to the artery/vein determination unit 73, as blood vessel aggregate detection information D2.

The artery/vein determination unit 73 performs artery/vein determination for each of the blood vessels in the blood vessel aggregate region included in the blood vessel aggregate detection information D2, and outputs the information representing a result of the artery/vein determination to the correction unit 74, as artery/vein determination information D3.

The correction unit 74 corrects the artery/vein determination result included in the blood vessel single-body detection information D1 based on the artery/vein determination information D3. The correction unit 74 outputs information including the corrected blood vessel single-body detection information D1, the blood vessel aggregate detection information D2, and the artery/vein determination information D3 to the highlight display unit 54, as the blood vessel detection information DB described above.

Figure 7:
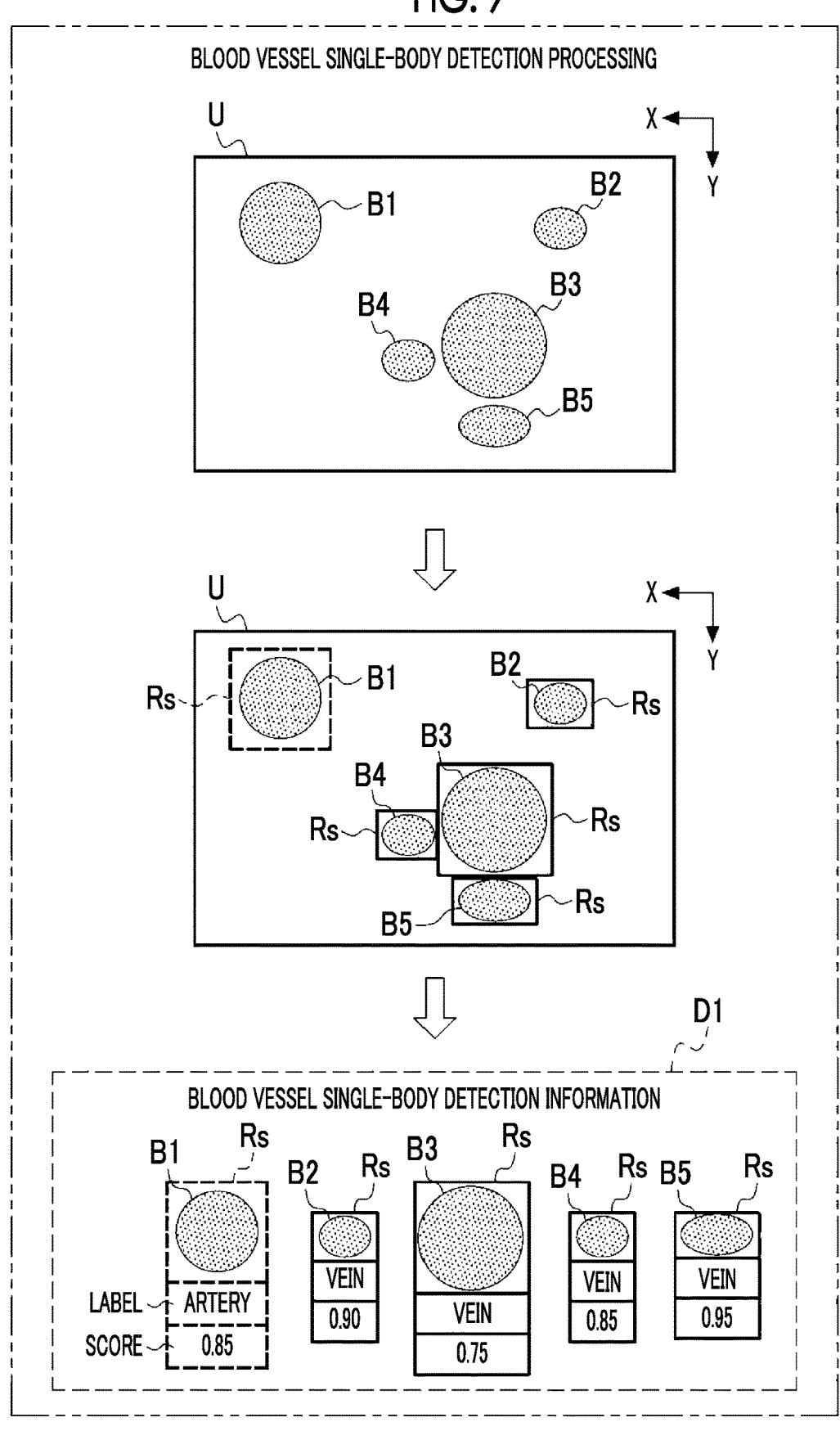
FIG. 7 is a diagram illustrating an example of blood vessel single-body detection processing.

FIG. 7 illustrates an example of blood vessel single-body detection processing by the blood vessel single-body detection unit 71. The blood vessel single-body detection unit 71 performs processing of detecting a blood vessel single-body region Rs including a blood vessel single-body from the ultrasound image U by using a known algorithm, and performs artery/vein determination. In FIG. 7, reference numerals B1 to B5 represent blood vessels. In the following, in a case where it is not necessary to distinguish blood vessels from each other, the blood vessels will be simply referred to as blood vessels B. The blood vessel single-body region Rs indicated by a broken line represents a region including a blood vessel B determined as an artery. The blood vessel single-body region Rs indicated by a solid line represents a region including a blood vessel B determined as a vein.

A "label" representing an artery/vein determination result and a "score" representing reliability (that is, certainty) of the artery/vein determination result are associated with the blood vessel single-body region Rs. The label represents whether the blood vessel B included in the blood vessel single-body region Rs is an "artery" or a "vein". The score is a value in a range equal to or larger than 0 and equal to or smaller than 1. As the score is closer to 1, the reliability is higher. The blood vessel single-body region Rs associated with the label and the score corresponds to the above-described blood vessel single-body detection information D1.

In the present embodiment, the blood vessel single-body detection unit 71 performs blood vessel single-body detection processing using a blood vessel single-body detection model 71A (refer to FIG. 8), which is a trained model generated by machine learning. The blood vessel single-body detection model 71A is, for example, an object detection algorithm using deep learning. As the blood vessel single-body detection model 71A, for example, an object detection model configured by regional CNN (R-CNN), which is a kind of convolutional neural network (CNN), can be used.

The blood vessel single-body detection model 71A detects, as an object, a region including a blood vessel single-body from the ultrasound image U, and determines a label for the detected region. In addition, the blood vessel single-body detection model 71A outputs information representing the detected blood vessel single-body region Rs together with a label and a score.

Figure 8:
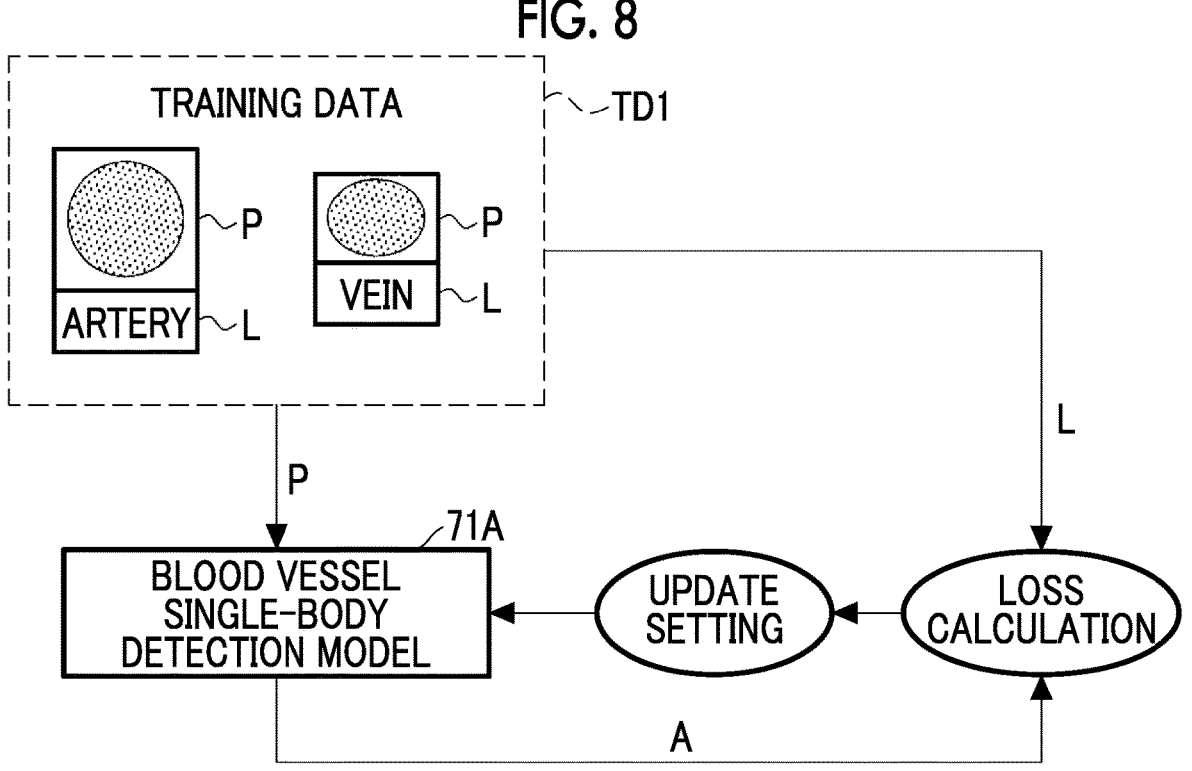
FIG. 8 is a diagram illustrating an example of a training phase in which a blood vessel single-body detection model is trained,

FIG. 8 is a diagram illustrating an example of a training phase in which the blood vessel single-body detection model 71A is trained by machine learning. The blood vessel single-body detection model 71A performs training using training data TD1. The training data TD1 includes a plurality of training images P associated with correct answer labels L. The training image P included in the training data TD1 is a sample image of a blood vessel single-body (artery and vein). The training data TD1 includes various training images P in which blood vessels have different shapes, sizes, and the like.

In the training phase, the training image P is input to the blood vessel single-body detection model 71A. The blood vessel single-body detection model 71A outputs a determination result A of the training image P. Loss calculation is performed using a loss function based on the determination result A and the correct answer label L. In addition, update setting of various coefficients of the blood vessel single-body detection model 71A is performed according to a result of the loss calculation, and the blood vessel single-body detection model 71A is updated according to the update setting.

In the training phase, a series of processing, which includes inputting of the training image P to the blood vessel single-body detection model 71A, outputting of the determination result A from the blood vessel single-body detection model 71A, the loss calculation, the update setting, and updating of the blood vessel single-body detection model 71A, is repeatedly performed. The repetition of the series of processing is ended in a case where detection accuracy reaches a predetermined setting level. The blood vessel single-body detection model 71A of which the detection accuracy reaches the setting level is stored in the storage device 24, and then is used by the blood vessel single-body detection unit 71 in the blood vessel single-body detection processing which is in an operation phase.

Figure 9:
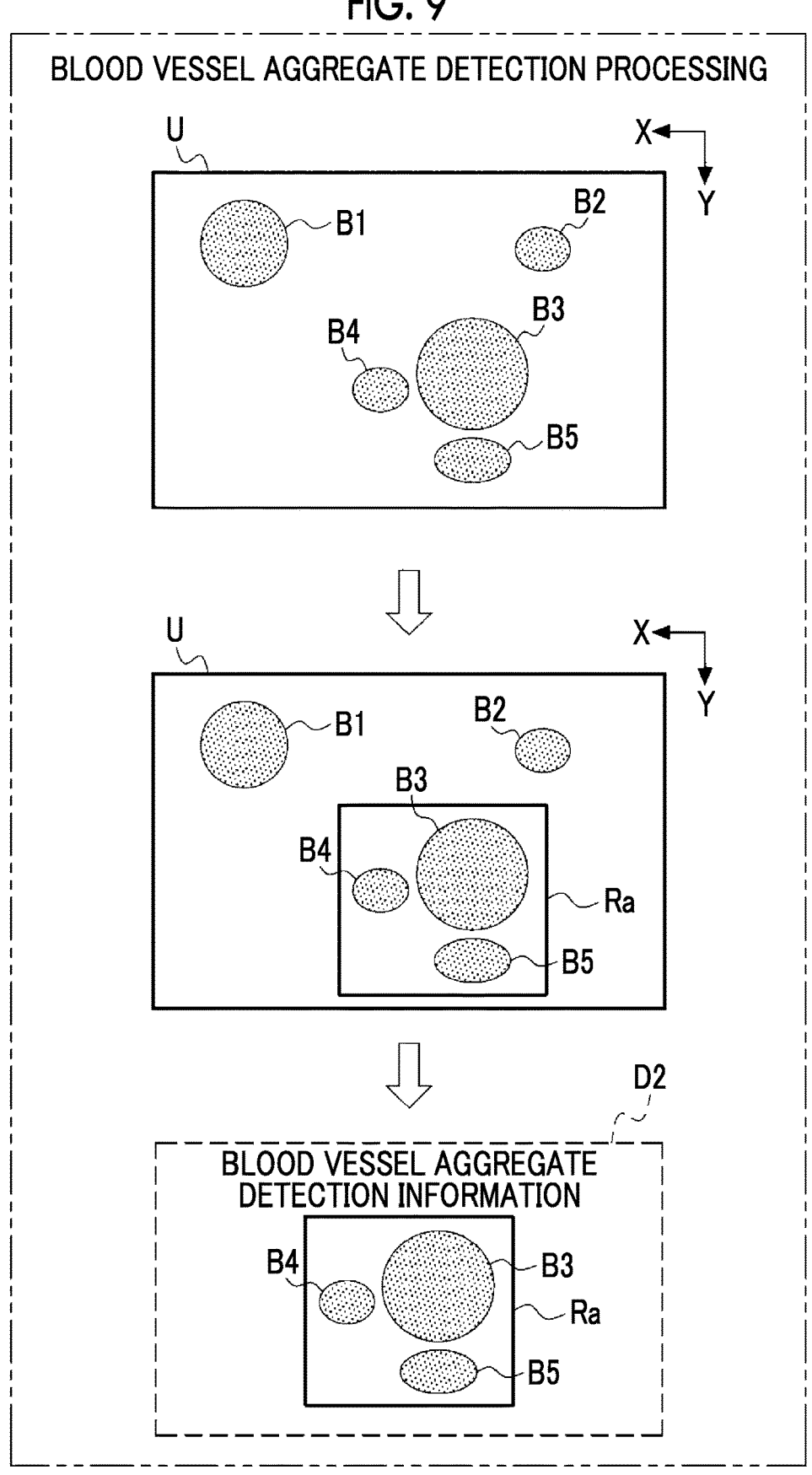
FIG. 9 is a diagram illustrating an example of blood vessel aggregate detection processing.

FIG. 9 illustrates an example of blood vessel aggregate detection processing by the blood vessel aggregate detection unit 72. The blood vessel aggregate detection unit 72 performs processing of detecting a blood vessel aggregate region Ra including a blood vessel aggregate from the ultrasound image U by using a known algorithm.

In the present embodiment, the blood vessel aggregate detection unit 72 performs blood vessel aggregate detection processing by using a blood vessel aggregate detection model 72A (refer to FIG. 10), which is a trained model generated by machine learning. The blood vessel aggregate detection model 72A is, for example, an object detection algorithm using deep learning. As the blood vessel aggregate detection model 72A, for example, an object detection model configured by R-CNN, which is a kind of CNN, can be used.

The blood vessel aggregate detection unit 72 detects, as an object, a blood vessel aggregate region Ra including a blood vessel aggregate from the ultrasound image U. The information representing the blood vessel aggregate region Ra corresponds to the blood vessel aggregate detection information D2 described above.

Figure 10:
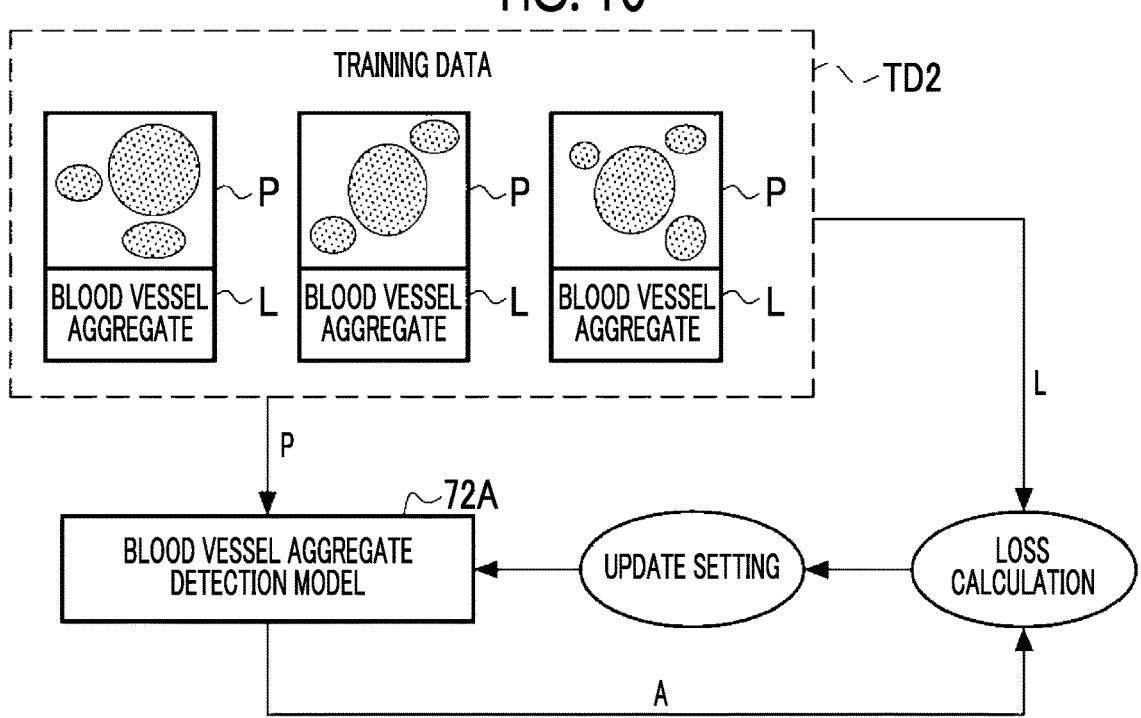
FIG. 10 is a diagram illustrating an example of a training phase in which a blood vessel aggregate detection model is trained,

FIG. 10 is a diagram illustrating an example of a training phase in which the blood vessel aggregate detection model 72A is trained by machine learning. The blood vessel aggregate detection model 72A performs training using training data TD2. The training data TD2 includes a plurality of training images P associated with correct answer labels L. The training image P included in the training data TD2 is a sample image of a blood vessel aggregate. The training data TD2 includes various training images P in which the number of the blood vessels, shapes of the blood vessels, sizes of the blood vessels, and arrangement (positional relationship) of a plurality of blood vessels are different in the blood vessel aggregate.

In the training phase, the training image P is input to the blood vessel aggregate detection model 72A. The blood vessel aggregate detection model 72A outputs a determination result A of the training image P. Loss calculation is performed using a loss function based on the determination result A and the correct answer label L. In addition, update setting of various coefficients of the blood vessel aggregate detection model 72A is performed according to a result of the loss calculation, and the blood vessel aggregate detection model 72A is updated according to the update setting.

In the training phase, a series of processing, which includes inputting of the training image P to the blood vessel aggregate detection model 72A, outputting of the determination result A from the blood vessel aggregate detection model 72A, the loss calculation, the update setting, and updating of the blood vessel aggregate detection model 72A, is repeatedly performed. The repetition of the series of processing is ended in a case where detection accuracy reaches a predetermined setting level. The blood vessel aggregate detection model 72A of which the detection accuracy reaches the setting level is stored in the storage device 24, and then is used by the blood vessel aggregate detection unit 72 in the blood vessel aggregate detection processing which is in an operation phase.

Figure 11:
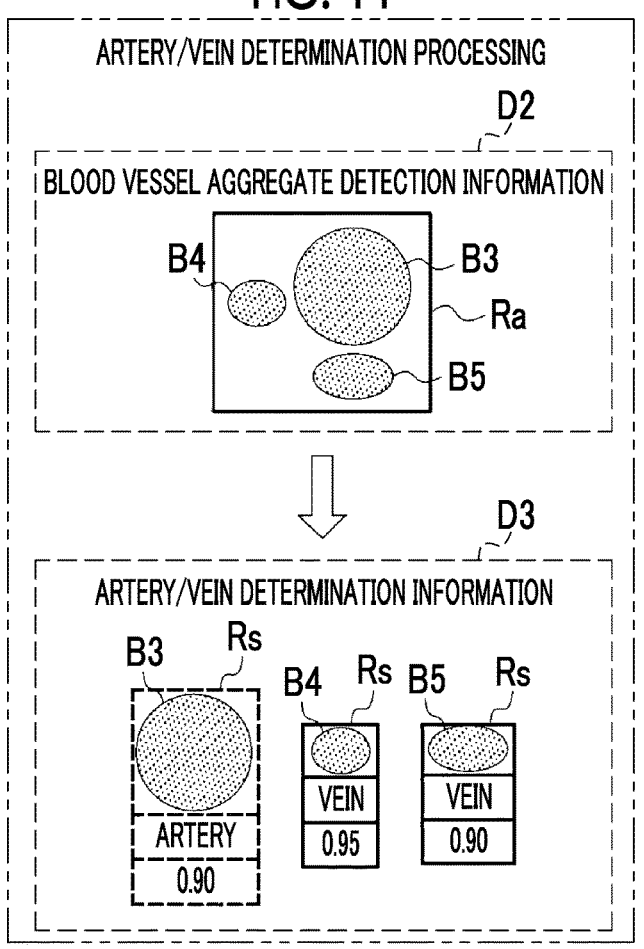
FIG. 11 is a diagram illustrating an example of artery/vein determination processing.

FIG. 11 illustrates an example of artery/vein determination processing by the artery/vein determination unit 73. The artery/vein determination unit 73 performs artery/vein determination for each of the blood vessels B included in the blood vessel aggregate region Ra based on the blood vessel aggregate detection information D2, and generates artery/vein determination information D3 by obtaining the label and the score for each of the blood vessels B. In the artery/vein determination, the artery/vein determination unit 73 uses anatomical feature amounts of the blood vessel in the blood vessel aggregate region Ra. The artery/vein determination unit 73 obtains, as a label for the blood vessel B, a score for each of "artery" and "vein", and selects the label having a higher score.

Figure 12:
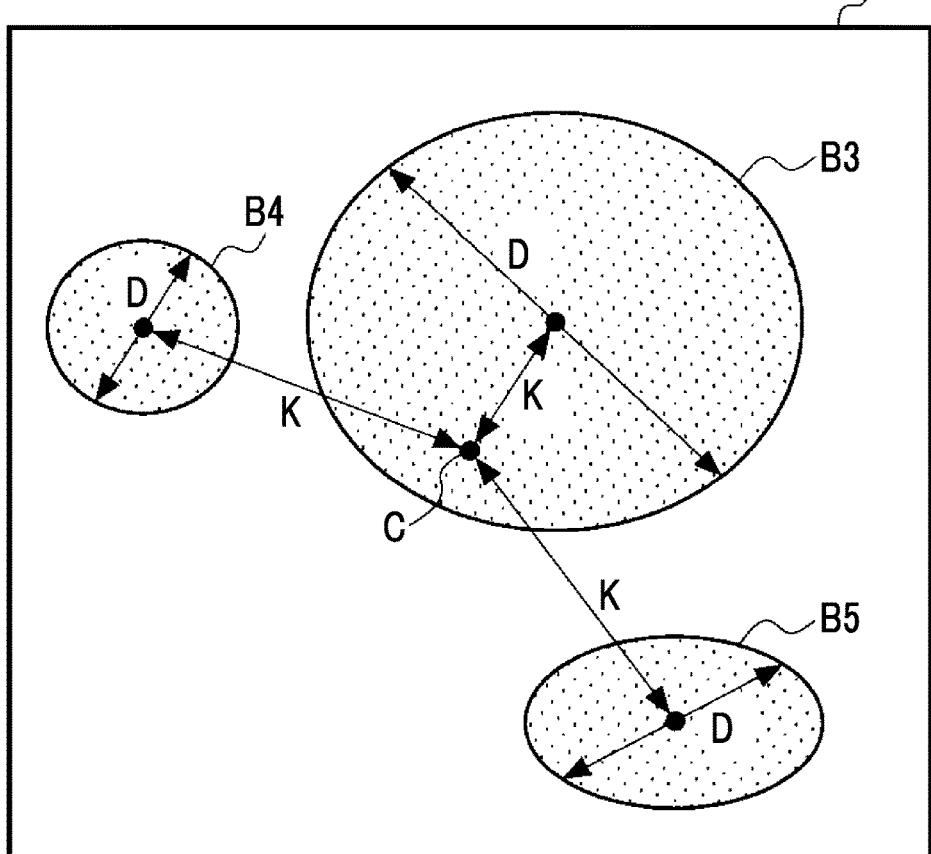
FIG. 12 is a diagram illustrating an example of artery/vein determination processing in more detail.
Figure 12:
Figure 12:

FIG. 12 is a diagram illustrating an example of the artery/vein determination processing in more detail. First, the artery/vein determination unit 73 calculates feature amounts for each of the blood vessels B included in the blood vessel aggregate region Ra. The feature amounts include a diameter (hereinafter, referred to as a blood vessel diameter) D of each blood vessel B in the blood vessel aggregate region Ra, a displacement amount K of the blood vessel B from the center C of the blood vessel aggregate region Ra, a circularity of each blood vessel B, and the like. The displacement amount K is, for example, a distance from the center C of the blood vessel aggregate region Ra to the center of each blood vessel B. The artery/vein determination unit 73 determines whether each of the blood vessels B is an artery or a vein by using the feature amounts of at least one or more of the blood vessel diameter D, the displacement amount K, or the circularity. The artery/vein determination unit 73 performs artery/vein determination by using, for example, an algorithm based on machine learning such as AdaBoost or support vector machine (SVM).

The artery is often located at the center of the blood vessel aggregate, and thus the displacement amount K is small. Further, an internal pressure in the artery is high. Thus, the artery has a large blood vessel diameter and a high circularity. On the other hand, the vein accompanies the artery, and thus the displacement amount K in the vein is large. Further, an internal pressure in the vein is low. Thus, the vein has a small blood vessel diameter and a low circularity. Based on these feature amounts, the artery/vein determination unit 73 performs artery/vein determination on each of the blood vessels B, and performs score calculation and label determination. For example, the artery/vein determination unit 73 calculates a score for an artery and a score for a vein for each of the blood vessels B, and selects the label having a higher score. In this way, the artery/vein determination can be performed with high accuracy by performing determination using the anatomical feature amounts for the blood vessel aggregate.

Figure 13:
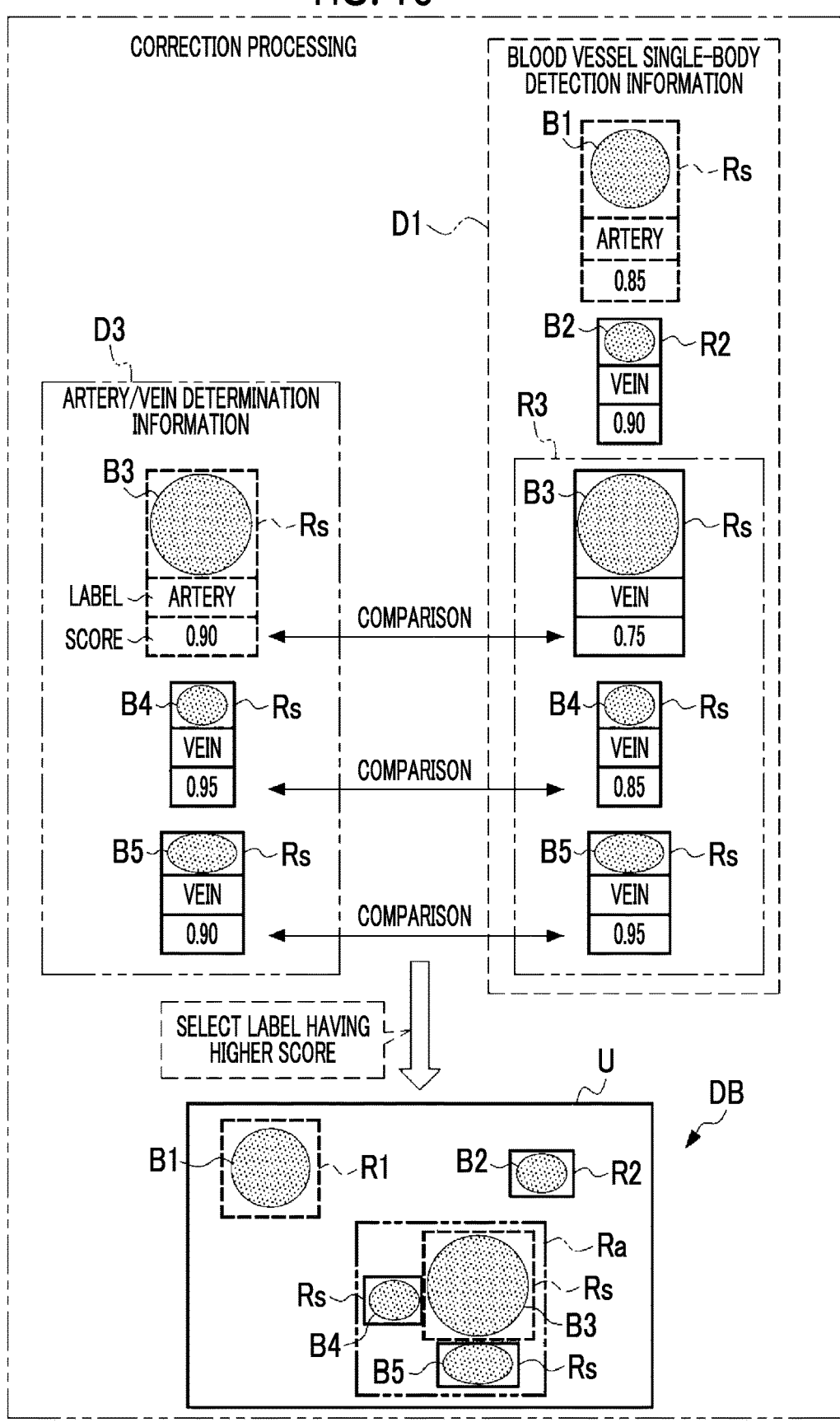
FIG. 13 is a diagram illustrating an example of correction processing.

FIG. 13 illustrates an example of correction processing performed by the correction unit 74. The correction unit 74 compares, for the corresponding blood vessel B, the score included in the artery/vein determination information D3 with the score included in the blood vessel single-body detection information D1, and selects the label having a higher score. For example, in the example illustrated in FIG. 13, for the blood vessel B3, the score (0.90) included in the artery/vein determination information D3 is higher than the score (0.75) included in the blood vessel single-body detection information D1. Therefore, the correction unit 74 selects, as the label of the blood vessel B3, the label (artery) included in the artery/vein determination information D3 instead of the label (vein) included in the blood vessel single-body detection information D1. Similarly, the correction unit 74 also selects, for the blood vessels B4 and B5, the label having a higher score. That is, in the example illustrated in FIG. 13, only the label of the blood vessel B3 is corrected among the labels of the blood vessels B1 to B5 included in the blood vessel single-body detection information D1. In this way, the label included in the blood vessel single-body detection information D1 is corrected.

The correction unit 74 outputs information including the corrected blood vessel single-body detection information D1 in which the label is corrected, the blood vessel aggregate detection information D2, and the artery/vein determination information D3 to the highlight display unit 54, as the blood vessel detection information DB described above. The blood vessel detection information DB includes position information of the blood vessel single-body region Rs and the blood vessel aggregate region Ra in the ultrasound image U, and the label and the score for the blood vessel single-body region Rs.

Figure 14:
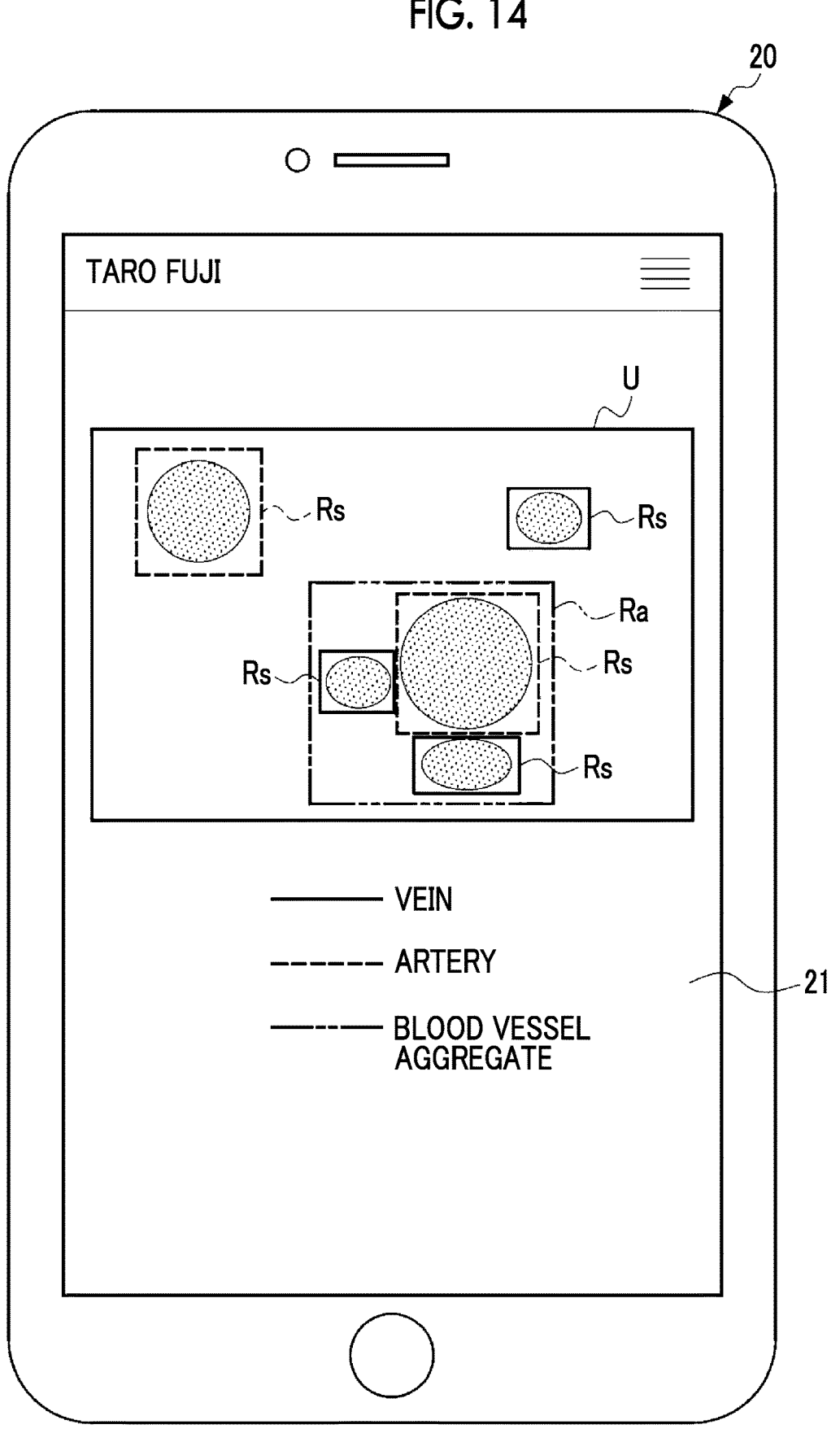
FIG. 14 is a diagram illustrating an example of highlight display processing.

FIG. 14 illustrates an example of highlight display processing by the highlight display unit 54. The highlight display unit 54 displays the blood vessel single-body region Rs and the blood vessel aggregate region Ra in the ultrasound image U displayed on the display device 21 of the apparatus main body 20 based on the blood vessel detection information DB by using a rectangular frame. In addition, the highlight display unit 54 displays the blood vessel single-body region Rs based on the artery/vein determination result such that the blood vessel included in the blood vessel single-body region Rs can be identified as an artery or a vein. In the example illustrated in FIG. 14, the blood vessel single-body region Rs including a vein is indicated by a solid line, and the blood vessel single-body region Rs including an artery is indicated by a broken line. In addition, the blood vessel aggregate region Ra is indicated by a two-dot chain line. The highlight display unit 54 may display the blood vessel single-body region Rs and the blood vessel aggregate region Ra such that the regions can be identified according to a thickness of a line, a color of a line, brightness of a line, or the like without being limited to the line type.

Figure 15:
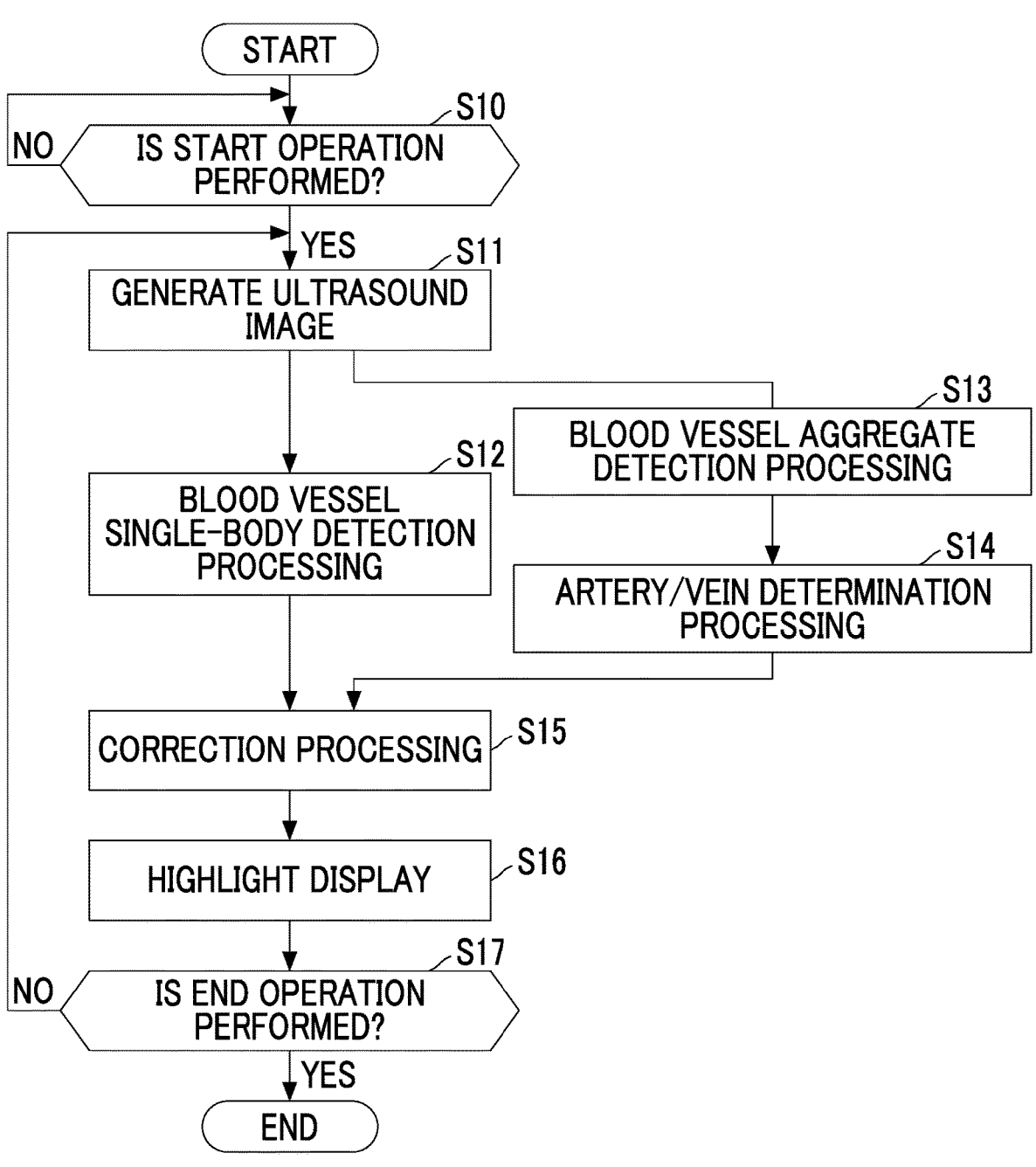
FIG. 15 is a flowchart illustrating an example of an operation of the ultrasound diagnostic apparatus,

Next, an example of an operation of the ultrasound diagnostic apparatus 2 will be described with reference to a flowchart illustrated in FIG. 15. First, the main control unit 50 determines whether or not a start operation is performed by the operator using the input device 22 or the like (step S10). In a case where it is determined that a start operation is performed (YES in step S10), the main control unit 50 generates the ultrasound image U by operating the transmission/reception circuit 14 of the ultrasound probe 10 and the image generation unit 51 (step S11). The generated ultrasound image U is displayed on the display device 21 by the display control unit 52.

At this time, as illustrated in FIG. 2, the operator brings the ultrasound probe 10 into contact with the surface of the living body 30. The ultrasound beams UBs are transmitted from the transducer array 13 into the living body 30 according to the drive signal which is input from the transmission circuit 16. The ultrasound echo from the living body 30 is received by the transducer array 13, and the received signal is output to the reception circuit 17. The received signal which is received by the reception circuit 17 is processed via the amplification unit 41, the A/D conversion unit 42, and the beam former 43, and thus a sound wave signal is generated. The sound wave signal is output to the apparatus main body 20 via the communication unit 15.

The apparatus main body 20 receives the sound wave signal which is output from the ultrasound probe 10 via the communication unit 23. The sound wave signal which is received by the apparatus main body 20 is input to the image generation unit 51. In the image generation unit 51, a B-mode image signal is generated by performing envelope detection processing on the sound wave signal by the signal processing unit 61, and the B-mode image signal is subjected to the DSC 62 and the image processing unit 63. Thus, an ultrasound image U is output to the display control unit 52. Further, the ultrasound image U is output to the image analysis unit 53.

In the image analysis unit 53, the blood vessel single-body detection processing (refer to FIG. 7) is performed by the blood vessel single-body detection unit 71 (step S12). The blood vessel single-body detection information D1 generated by the blood vessel single-body detection processing is output to the correction unit 74.

In addition, step S13 and step S14 are performed in parallel with step S12. In step S13, the blood vessel aggregate detection processing (refer to FIG. 9) is performed by the blood vessel aggregate detection unit 72. The blood vessel aggregate detection information D2 generated by the blood vessel aggregate detection processing is output to the artery/vein determination unit 73. In step S14, the artery/ vein determination processing (refer to FIG. 11 and FIG. 12) is performed by the artery/vein determination unit 73. The artery/vein determination information D3 generated by the artery/vein determination processing is output to the correction unit 74.

Further, in the image analysis unit 53, the correction processing (refer to FIG. 13) is performed by the correction unit 74 (step S15). In the correction processing, the label for the blood vessel single-body region Rs included in the blood vessel single-body detection information D1 is corrected based on the artery/vein determination information D3. As a result of the correction processing, the blood vessel detection information DB is output to the highlight display unit 54.

In addition, the highlight display processing (refer to FIG. 14) is performed by the highlight display unit 54 (step S16). By the highlight display processing, the blood vessel single-body region Rs and the blood vessel aggregate region Ra are highlighted and displayed in the ultrasound image U displayed on the display device 21. In addition, the blood vessel single-body region Rs is displayed such that the blood vessel included in the blood vessel single-body region Rs can be identified as an artery or a vein. In this way, by performing highlight display, the operator can accurately recognize the blood vessel aggregate in the ultrasound image U, and can accurately recognize whether the blood vessel single-body is an artery or a vein.

Next, the main control unit 50 determines whether or not an end operation is performed by the operator using the input device 22 or the like (step S17). In a case where it is determined that an end operation is not performed (NO in step S17), the main control unit 50 returns the processing to step S11. Thereby, a new ultrasound image U is generated. On the other hand, in a case where it is determined that an end operation is performed (YES in step S17), the main control unit 50 ends the operation of the ultrasound diagnostic apparatus 2.

In the related art, a blood vessel is detected by blood vessel single-body detection processing, and artery/vein determination is individually performed on the detected blood vessel. In such a method, an error often occurs in the artery/vein determination of the blood vessels included in the blood vessel aggregate, and a result of the artery/vein determination may change for each frame. In a case where the operator attempts to perform puncture based on the result of the artery/vein determination, the blood vessel to be punctured may be mistaken.

On the other hand, according to the technique of the present disclosure, the blood vessel aggregate region Ra is detected from the ultrasound image U, and the detected blood vessel aggregate region Ra is highlighted and displayed in the ultrasound image U. Thus, it is possible to support artery/vein determination of the blood vessel by the operator. In addition, according to the technique of the present disclosure, artery/vein determination is performed based on the feature amounts of the blood vessel in the blood vessel aggregate region Ra. Thus, it is possible to perform artery/vein determination with high accuracy even for the blood vessel included in the blood vessel aggregate. Thereby, the operator can accurately recognize the blood vessel (for example, a vein) to be punctured.

MODIFICATION EXAMPLE

Hereinafter, various modification examples of the ultrasound diagnostic apparatus 2 according to the first embodiment will be described.

Figure 16:
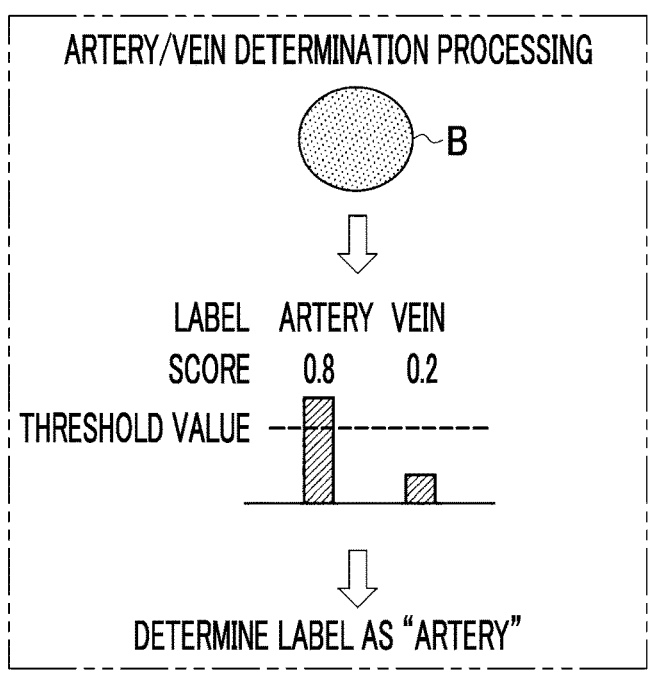
FIG. 16 is a diagram illustrating a modification example of artery/vein determination processing.

In the first embodiment, the artery/vein determination unit 73 obtains, as the label for the blood vessel B, a score for each of "artery" and "vein" in the artery/vein determination processing (refer to FIG. 11 and FIG. 12), and selects the label having a higher score. Instead, for example, as illustrated in FIG. 16, a threshold value for a score may be set, and a label having a score equal to or higher than the threshold value may be selected.

Figure 17:
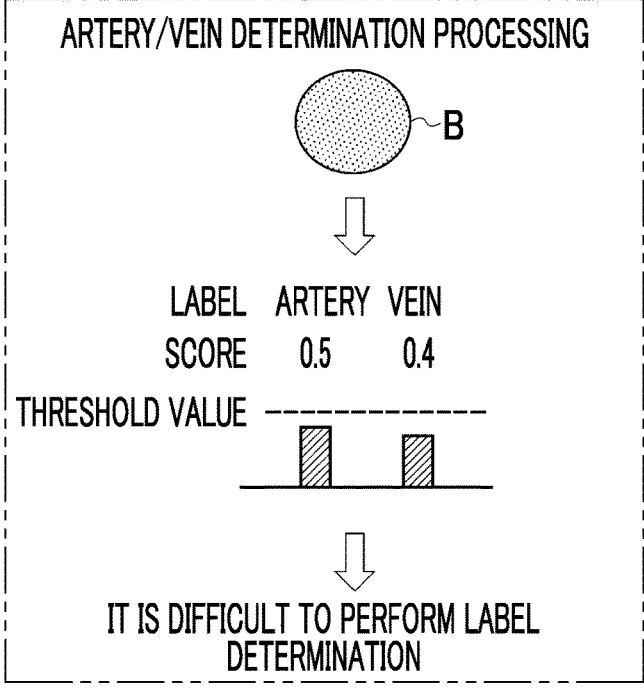
FIG. 17 is a diagram illustrating a modification example of artery/vein determination processing.
Figure 18:
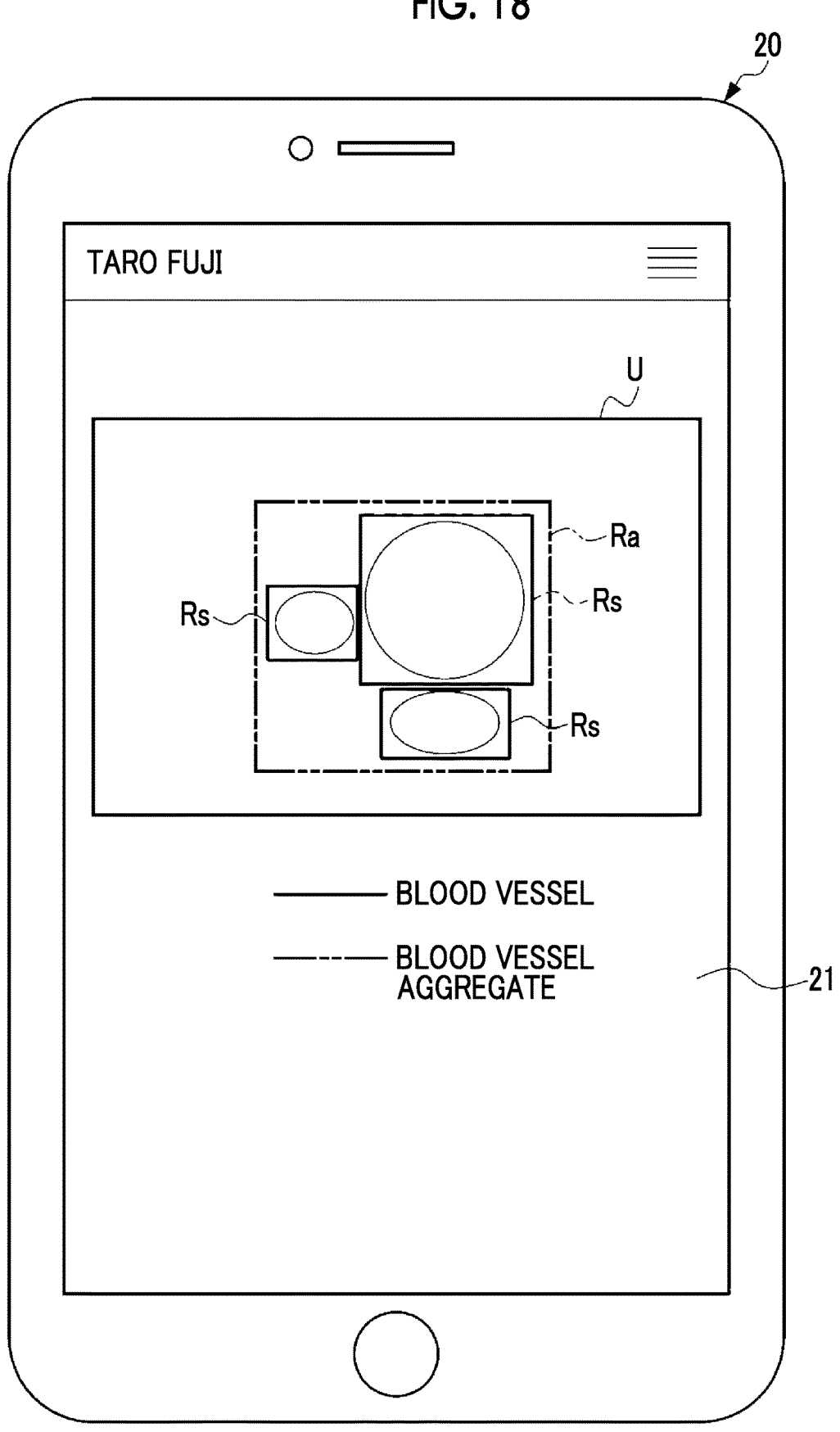
FIG. 18 is a diagram illustrating a modification example 60 of highlight display.

In addition, for example, as illustrated in FIG. 17, in a case where the score is obtained for each of "artery" and "vein" as the label for the blood vessel B, both scores may be lower than the threshold value. In this case, it is difficult to perform label determination (that is, artery/vein determination). Thus, the artery/vein determination unit 73 may stop artery/vein determination. In such a case where it is difficult to perform artery/vein determination, the highlight display unit 54 may display the blood vessel single-body region Rs in the ultrasound image U without distinguishing whether the blood vessel single-body region Rs is an "artery" or a "vein". In this case, the highlight display unit 54 may simply display the blood vessel single-body region Rs, for example, as a "blood vessel", as illustrated in FIG. 18.

Figure 19:
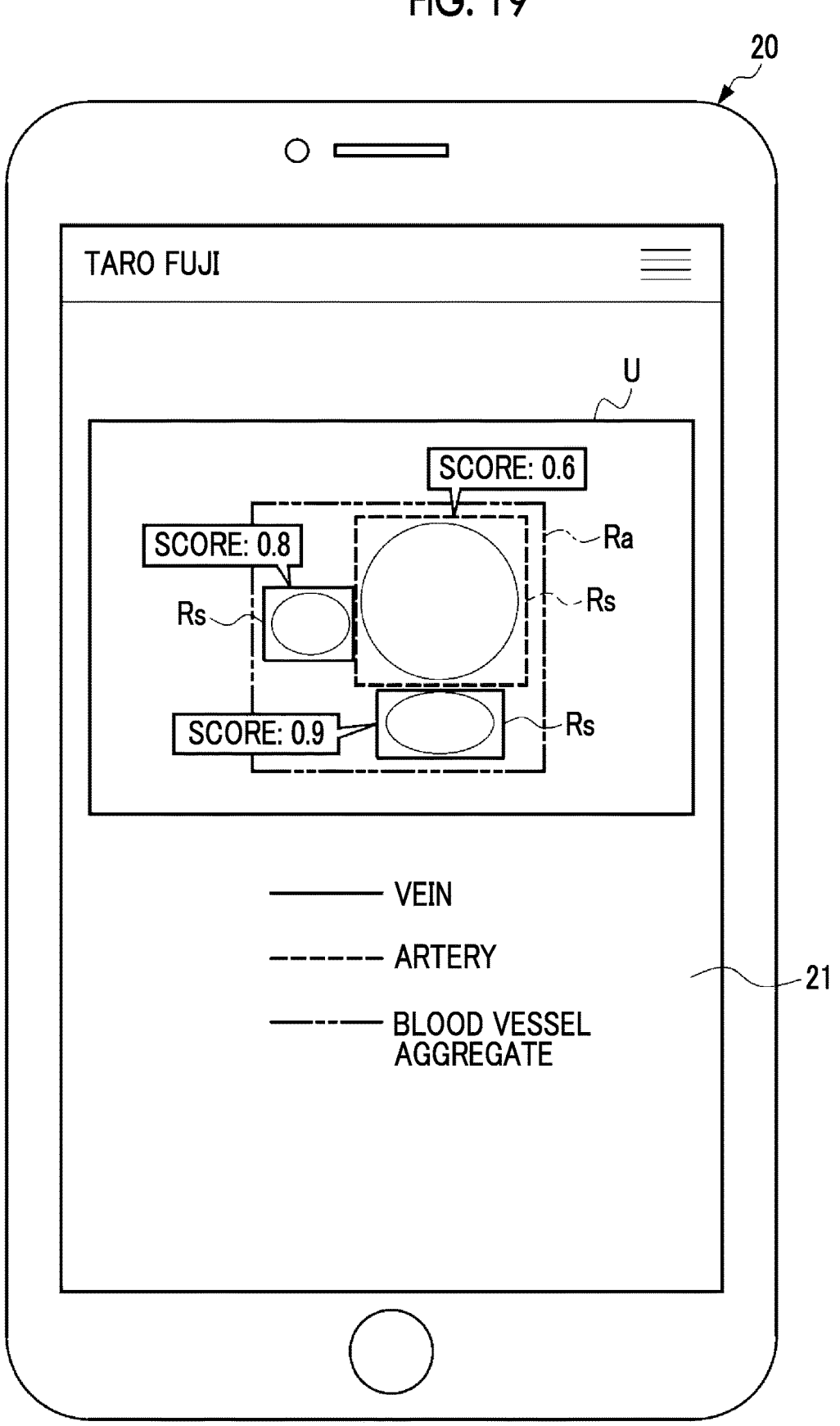
FIG. 19 is a diagram illustrating an example of displaying a score.

In addition, as illustrated in FIG. 19, for example, the highlight display unit 54 may display the score for the label selected by the correction unit 74 (that is, reliability for the determination result selected by the correction unit 74) in association with the blood vessel single-body region Rs. Thereby, the operator can recognize the reliability of the artery/vein determination for each blood vessel.

Figure 20:
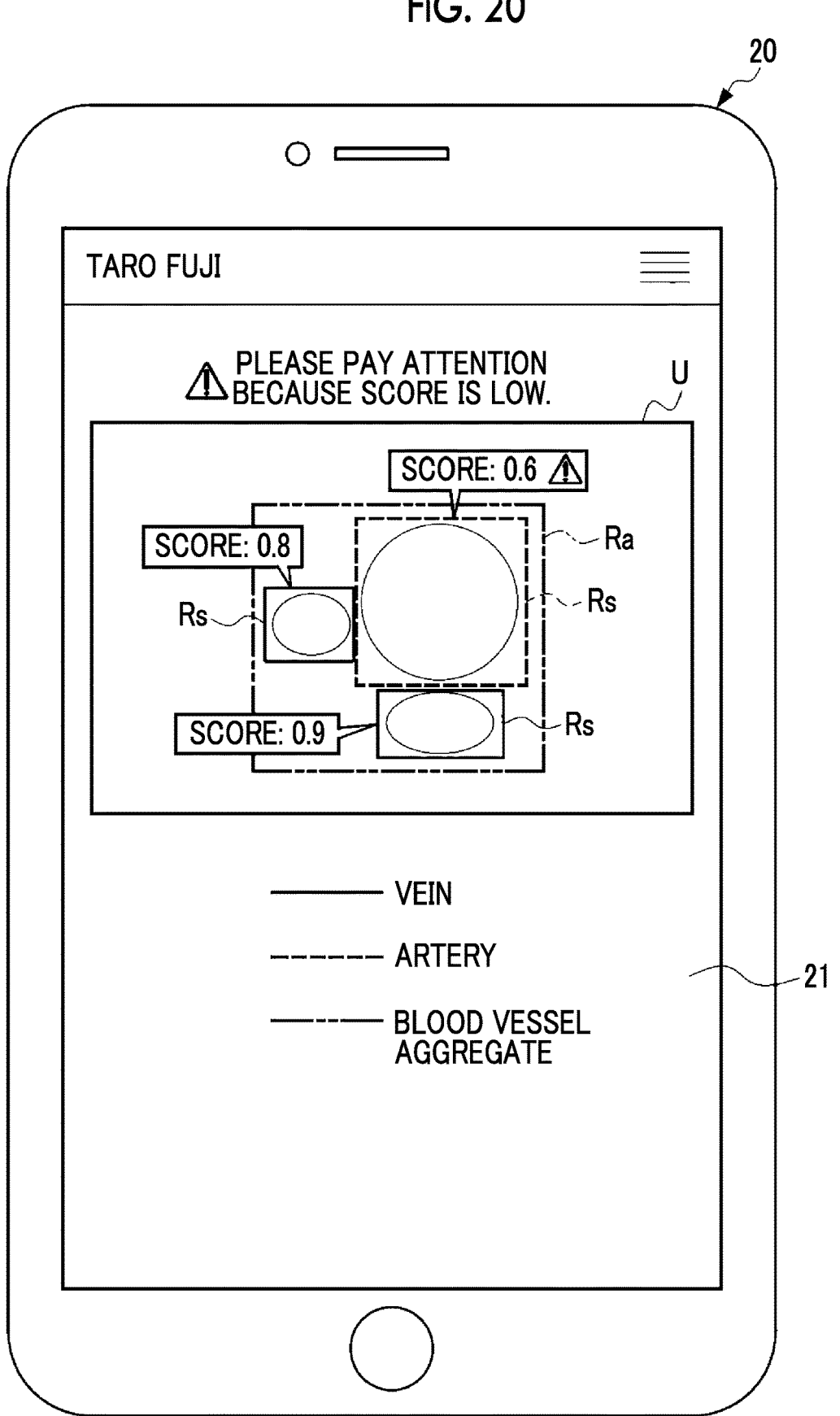
FIG. 20 is a diagram illustrating an example of displaying a message urging an operator to pay attention,

In addition, as illustrated in FIG. 20, for example, the highlight display unit 54 may display a message urging the operator to pay attention in a case where the score for the label selected by the correction unit 74 (that is, reliability for the determination result selected by the correction unit 74)

is lower than a certain value. Thereby, the operator can reliably recognize that reliability of the artery/vein determination is low and caution is required in the puncture.

In addition, the artery/vein determination unit 73 may change a criterion for artery/vein determination for each of the blood vessel aggregate regions Ra. This is because, for example, in a case where a pattern of the blood vessel aggregate in the blood vessel aggregate region Ra is an anatomically typical pattern, there is a high possibility that the determination result is correct even though the score of the artery/vein determination is low. The pattern of the blood vessel aggregate is information represented by a relative position of the plurality of blood vessels of the blood vessel aggregate, the number of the blood vessels, the size of each blood vessel, and the like.

Figure 21:
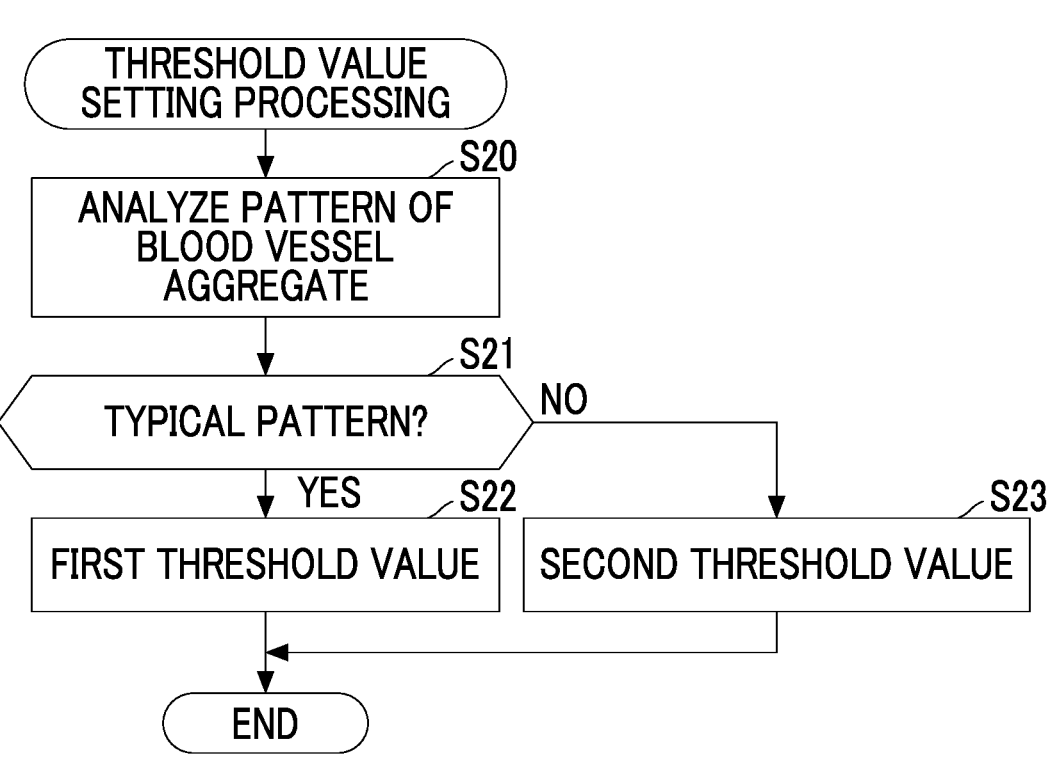
FIG. 21 is a flowchart illustrating an example of threshold value setting processing.

The artery/vein determination unit 73 performs, for example, threshold value setting processing illustrated in FIG. 21 before performing artery/vein determination on the blood vessel aggregate region Ra. First, the artery/vein determination unit 73 analyzes a pattern of the blood vessel aggregate in the blood vessel aggregate region Ra (step S20), and determines whether or not the blood vessel aggregate is a typical pattern (step S21). In a case where it is determined that the blood vessel aggregate is a typical pattern (YES in step S21), the artery/vein determination unit 73 sets a threshold value for the artery/vein determination to a "first threshold value" (step S22). On the other hand, in a case where it is determined that the blood vessel aggregate is an atypical pattern (NO in step S21), the artery/vein determination unit 73 sets a threshold value for the artery/vein determination to a "second threshold value" (step S23). Here, the first threshold value is a value smaller than the second threshold value.

Figure 22:
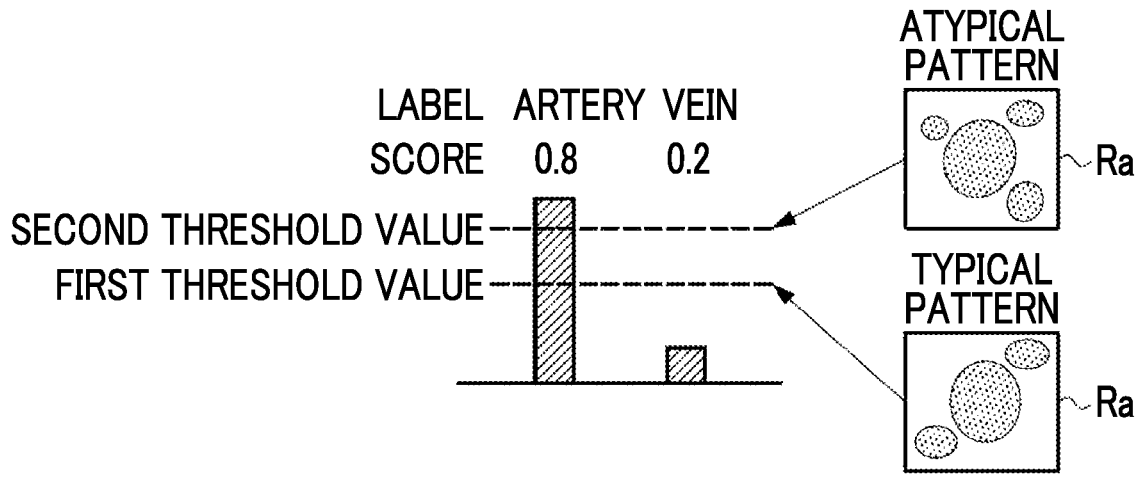
FIG. 22 is a diagram illustrating an example of a threshold value which is set by threshold value setting processing.

As illustrated in FIG. 22, in a case where the pattern of the blood vessel aggregate in the blood vessel aggregate region Ra is typical, the threshold value, which is a criterion for the artery/vein determination, is set to be low. On the other hand, in a case where the pattern of the blood vessel aggregate is atypical, the threshold value, which is a criterion for the artery/vein determination, is set to be high. In this way, in a case where the pattern of the blood vessel aggregate is atypical, the criterion for the artery/vein determination is set to be high, and thus the determination is more reliably performed. The criterion for the artery/vein determination is not limited to the threshold value for the score, and may be changed by changing the algorithm for the artery/vein determination.

Figure 23:
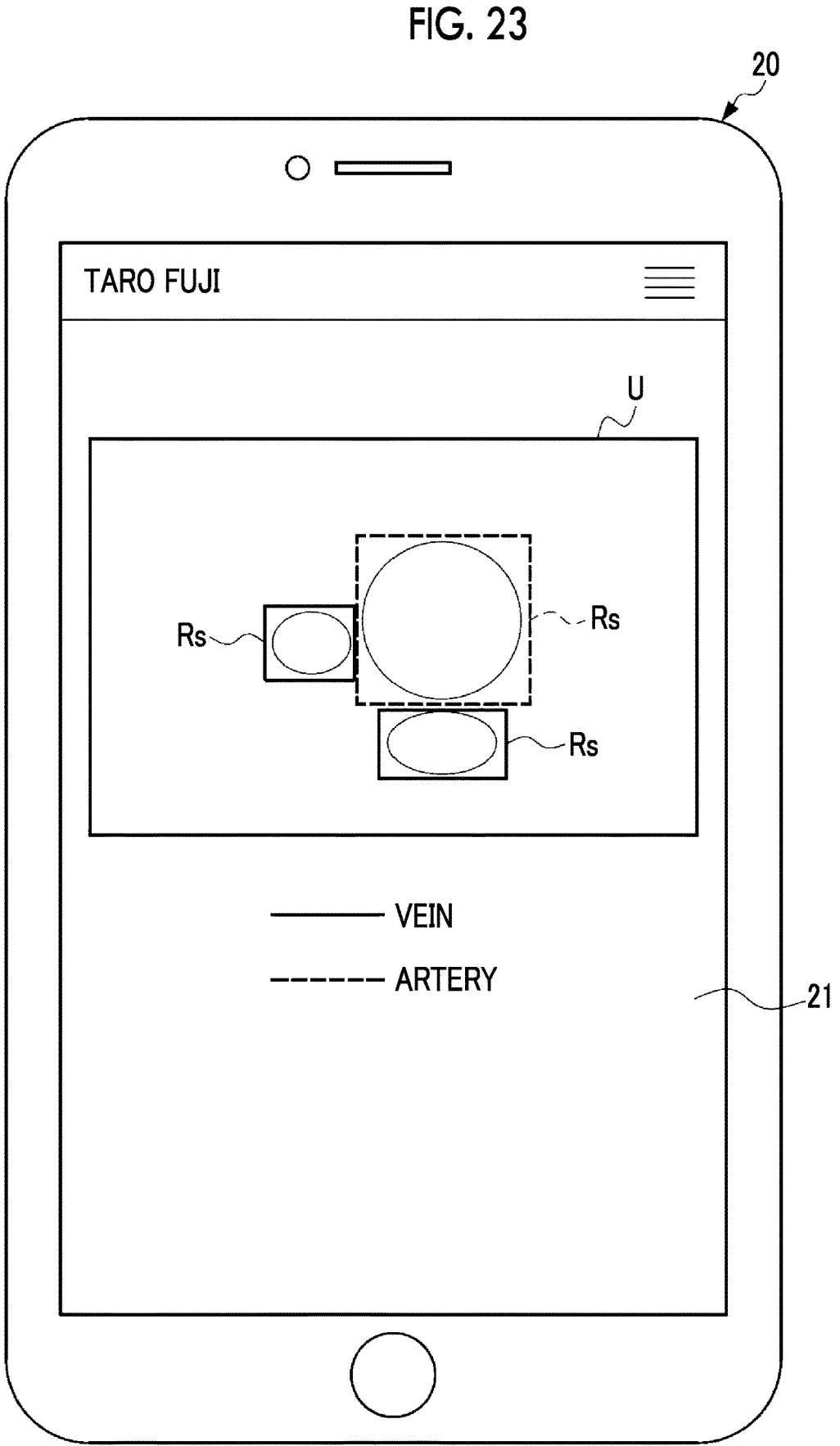
FIG. 23 is a diagram illustrating an example in which a blood vessel aggregate region is hidden.

In addition, as illustrated in FIG. 23, after the artery/vein determination unit 73 performs the artery/vein determination, the highlight display unit 54 may hide the blood vessel aggregate region Ra.

In addition, in the first embodiment, the blood vessel single-body detection unit 71 and the blood vessel aggregate detection unit 72 are respectively configured by individual object detection models. On the other hand, the blood vessel single-body detection unit 71 and the blood vessel aggregate detection unit 72 can be configured by one object detection model. In this case, the object detection model may be trained using training data including a training image of the blood vessel single-body and a training image of the blood vessel aggregate. In addition, the blood vessel single-body detection unit 71, the blood vessel aggregate detection unit 72, and the artery/vein determination unit 73 can be configured by one object detection model. Further, the blood vessel single-body detection unit 71, the blood vessel aggregate detection unit 72, the artery/vein determination unit 73, and the correction unit 74 can be configured by one object detection model.

In addition, in the first embodiment, the blood vessel single-body detection unit 71 and the blood vessel aggregate detection unit 72 are configured by an object detection model of a CNN. On the other hand, the object detection model is not limited to the CNN, and segmentation or another general detection model may be used.

In addition, the object detection model including the blood vessel single-body detection unit 71 and the blood vessel aggregate detection unit 72 may be configured by an identifier that identifies an object based on image feature amounts such as AdaBoost or SVM. In this case, after the training image is converted into a feature amount vector, the identifier may be trained based on the feature amount vector. As the feature amounts of the blood vessel aggregate, a distance between the blood vessels (a distance between the centers of the blood vessels, a distance between the outer peripheral portions of the blood vessels, and the like) can be used. The identifier recognizes that the object is a blood vessel aggregate in a case where the distance between the blood vessels is equal to or smaller than a certain value and the number of the blood vessels is 3 or more.

In addition, the blood vessel single-body detection unit 71 and the blood vessel aggregate detection unit 72 are not limited to the object detection model by machine learning, and may perform object detection by template matching. In this case, the blood vessel single-body detection unit 71 stores, as a template, typical pattern data of a blood vessel single-body in advance, and calculates a similarity to the pattern data while searching for the ultrasound images U by using the template. In addition, the blood vessel single-body detection unit 71 specifies, as a blood vessel single-body region Rs, a portion where the similarity is equal to or higher than a certain level and is maximized. Further, the blood vessel aggregate detection unit 72 stores, as a template, typical pattern data of a blood vessel aggregate in advance, and calculates a similarity to the pattern data while searching for the ultrasound images U by using the template. In addition, the blood vessel aggregate detection unit 72 specifies, as a blood vessel aggregate region Ra, a portion where the similarity is equal to or higher than a certain level and is maximized. The template may be a part of an actual ultrasound image, or may be an image drawn by modeling blood vessels or blood vessel aggregates.

Further, in order to calculate the similarity, in addition to simple template matching, for example, a machine learning method, which is described in Csurka et al.: Visual Categorization with Bags of Keypoints, Proc. of ECCV Workshop on Statistical Learning in Computer Vision, pp. 59-74 (2004), or a general image recognition method using deep learning, which is described in Krizhevsk et al.: ImageNet Classification with Deep Convolutional Neural Networks, Advances in Neural Information Processing Systems 25, pp. 1106-1114 (2012), can be used.

In the first embodiment, the ultrasound probe 10 and the apparatus main body 20 are connected by wireless communication. Instead, the ultrasound probe 10 and the apparatus main body 20 may be connected by wire.

Further, in the first embodiment, the image generation unit 51 that generates an ultrasound image U based on the sound wave signal is provided in the apparatus main body 20. Instead, the image generation unit 51 may be provided in the ultrasound probe 10. In this case, the ultrasound probe 10 generates an ultrasound image U and outputs the ultrasound image U to the apparatus main body 20. The processor 25 of the apparatus main body 20 performs image analysis or the like based on the ultrasound image U which is input from the ultrasound probe 10.

Further, in the first embodiment, the display device 21, the input device 22, and the ultrasound probe 10 are directly connected to the processor 25. On the other hand, the display device 21, the input device 22, and the ultrasound probe 10 may be indirectly connected to the processor 25 via a network.

Figures 24, 25:
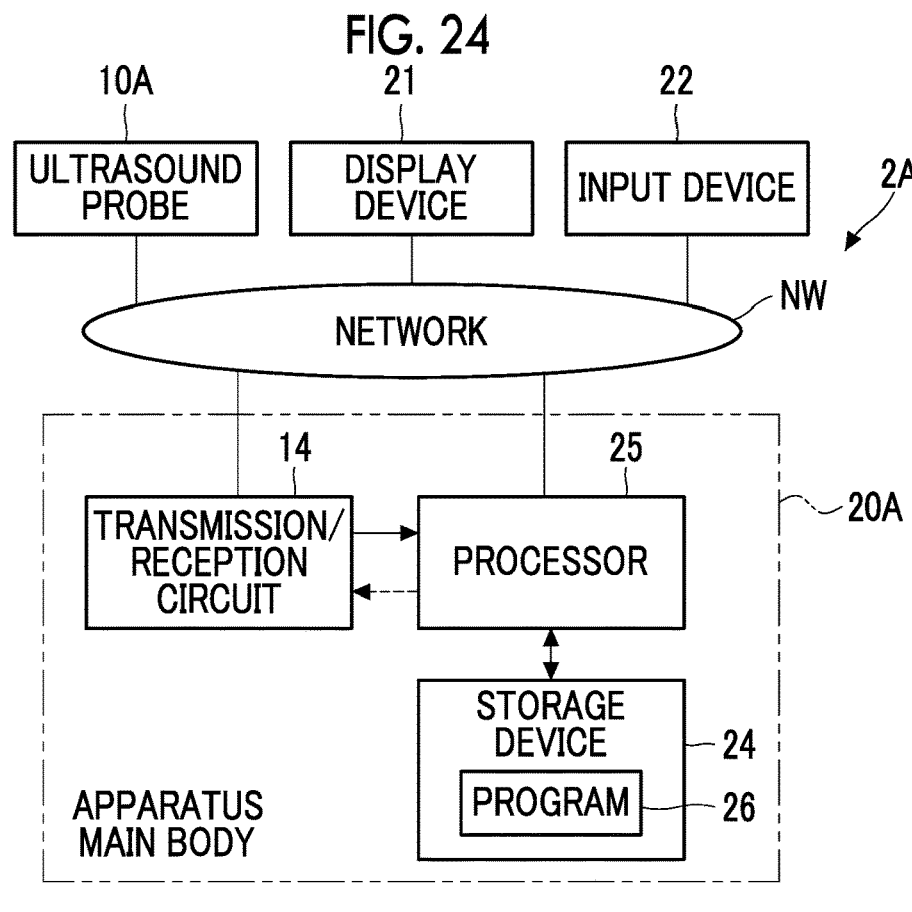
FIG. 24 is a diagram illustrating a first modification example of the ultrasound diagnostic apparatus.
FIG. 25 is a diagram illustrating a second modification example of the ultrasound diagnostic apparatus.

As an example, in the ultrasound diagnostic apparatus 2A illustrated in FIG. 24, the display device 21, the input device 22, and the ultrasound probe 10A are connected to the apparatus main body 20A via a network NW. The apparatus main body 20A is obtained by removing the display device 21 and the input device 22 from the apparatus main body 20 according to the first embodiment and adding the transmission/reception circuit 14, and is configured by the transmission/reception circuit 14, the storage device 24, and the processor 25. The ultrasound probe 10A is obtained by removing the transmission/reception circuit 14 from the ultrasound probe 10 according to the first embodiment.

In this way, in the ultrasound diagnostic apparatus 2A, the display device 21, the input device 22, and the ultrasound probe 10A are connected to the apparatus main body 20A via the network NW, and thus the apparatus main body 20A can be used as a so-called remote server. Thereby, for example, the operator can prepare the display device 21, the input device 22, and the ultrasound probe 10A at the operator's hand, and thus convenience is improved. In addition, in a case where the display device 21 and the input device 22 are configured by a mobile terminal such as a smartphone or a tablet terminal, convenience is further improved.

As another example, in the ultrasound diagnostic apparatus 2B illustrated in FIG. 25, the display device 21 and the input device 22 are provided in the apparatus main body 20B, and the ultrasound probe 10A is connected to the apparatus main body 20B via the network NW. In this case, the apparatus main body 20B may be configured by a remote server. In addition, the apparatus main body 20B can be configured by a mobile terminal such as a smartphone or a tablet terminal.

In the first embodiment, for example, the following various processors may be used as a hardware structure of processing units that perform various processing, such as the main control unit 50, the image generation unit 51, the display control unit 52, the image analysis unit 53, and the highlight display unit 54. The various processors include, as described above, a CPU which is a general-purpose processor that functions as various processing units by executing software (program 26), and a dedicated electric circuit which is a processor having a circuit configuration specifically designed to execute specific processing, such as a programmable logic device (PLD) or an ASIC that is a processor of which the circuit configuration may be changed after manufacturing such as a field programmable gate array (FPGA).

One processing unit may be configured by one of these various processors, or may be configured by a combination of two or more processors having the same type or different types (for example, a combination of a plurality of FPGAs and/or a combination of a CPU and an FPGA). Further, the plurality of processing units may be configured by one processor.

As an example in which the plurality of processing units are configured by one processor, firstly, as represented by a computer such as a client and a server, a form in which one processor is configured by a combination of one or more CPUs and software and the processor functions as the plurality of processing units may be adopted. Secondly, as represented by a system on chip (SoC) or the like, a form in which a processor that realizes the function of the entire system including the plurality of processing units by one IC chip is used may be adopted. As described above, the various processing units are configured by using one or more various processors as a hardware structure.

Further, as the hardware structure of the various processors, more specifically, an electric circuit (circuitry) in which circuit elements such as semiconductor elements are combined may be used.

From the above description, the technique described in following Appendixes 1 to 9 can be understood.

[Appendix 1]

An information processing apparatus that performs processing of causing a display device to display an ultrasound image, which is generated by transmitting ultrasound beams from a transducer array toward the inside of a living body and receiving ultrasound echoes generated in the living body, the apparatus including:

a processor, in which the processor is configured to:

detect, from the ultrasound image, a blood vessel aggregate region including a blood vessel aggregate in which three or more blood vessels are aggregated, and highlight and display the detected blood vessel aggregate region in the ultrasound image.

[Appendix 2]

The information processing apparatus according to Appendix 1, in which the processor is configured to determine whether each of the blood vessels included in the blood vessel aggregate region is an artery or a vein based on feature amounts of each blood vessel in the blood vessel aggregate region.

[Appendix 3]

The information processing apparatus according to Appendix 2, in which the processor is configured to perform determination based on at least one or more feature amounts of a blood vessel diameter, a displacement amount of the blood vessel from a center of the blood vessel aggregate region, or a circularity of the blood vessel.

[Appendix 4]

The information processing apparatus according to Appendix 2 or Appendix 3, in which the processor is configured to detect a blood vessel single-body region including a blood vessel single-body from the ultrasound image and determine whether the blood vessel included in the detected blood vessel single-body region is an artery or a vein.

[Appendix 5]

The information processing apparatus according to Appendix 4, in which the processor is configured to correct a result of artery/vein determination on the blood vessel in the blood vessel single-body region based on a result of artery/vein determination on each of the blood vessels in the blood vessel aggregate region.

[Appendix 6]

The information processing apparatus according to Appendix 5, in which the processor is configured to compare reliability of artery/vein determination on the blood vessel in the blood vessel single-body region with reliability of artery/vein determination on each of the blood vessels in the blood vessel aggregate region, and select a determination result having higher reliability.

[Appendix 7]

The information processing apparatus according to Appendix 6, in which the processor is configured to display each of the blood vessels included in the blood vessel aggregate region such that an artery and a vein can be identified from each other based on a correction result.

[Appendix 8]

The information processing apparatus according to Appendix 7, in which the processor is configured to display, on the display device, reliability on the selected determination result.

[Appendix 9]

The information processing apparatus according to Appendix 8, in which the processor is configured to display, on the display device, a message urging an operator to pay attention in a case where the reliability on the selected determination result is lower than a certain value.

The technique of the present disclosure can also appropriately combine the various embodiments and/or the various modification examples. In addition, the technique of the present disclosure is not limited to the embodiments, and various configurations may be adopted without departing from the scope of the present disclosure.

The described contents and the illustrated contents are detailed explanations of a part according to the technique of the present disclosure, and are merely examples of the technique of the present disclosure. For example, the descriptions related to the configuration, the function, the operation, and the effect are descriptions related to examples of a configuration, a function, an operation, and an effect of a part according to the technique of the present disclosure. Therefore, it goes without saying that, in the described contents and illustrated contents, unnecessary parts may be deleted, new components may be added, or replacements may be made without departing from the spirit of the technique of the present disclosure. Further, in order to avoid complications and facilitate understanding of the part according to the technique of the present disclosure, in the described contents and illustrated contents, descriptions of technical knowledge and the like that do not require particular explanations to enable implementation of the technique of the present disclosure are omitted.

In the present specification, "A and/or B" is synonymous with "at least one of A or B." That is, "A and/or B" means that only A may be included, that only B may be included, or that a combination of A and B may be included.

All documents, patent applications, and technical standards mentioned in this specification are incorporated herein by reference to the same extent as in a case where each document, each patent application, and each technical standard are specifically and individually described by being incorporated by reference.

What is claimed is:

1. An information processing apparatus that performs processing of causing a display device to display an ultrasound image, which is generated by transmitting ultrasound beams from a transducer array toward the inside of a living body and receiving ultrasound echoes generated in the living body, the apparatus including:

a processor, in which the processor is configured to:

detect, from the ultrasound image, a blood vessel aggregate region including a blood vessel aggregate in which three or more blood vessels are aggregated, the blood vessel aggregate comprising at least one artery and at least one vein, wherein the blood vessel aggregate region is a limited region within the ultrasound image, highlight and display the detected blood vessel aggregate region in the ultrasound image, calculate a displacement amount of each of the blood vessels from a center of the blood vessel aggregate region, and determine whether each of the blood vessels is an artery or a vein based on the calculation.

2. The information processing apparatus according to claim 1, wherein the processor is configured to calculate one or both of a blood vessel diameter or a circularity of the blood vessel.

3. The information processing apparatus according to claim 1, in which the processor is configured to detect a blood vessel single-body region including a blood vessel single-body from the ultrasound image and determine whether the blood vessel included in the detected blood vessel single-body region is an artery or a vein.

4. The information processing apparatus according to claim 3, in which the processor is configured to correct a result of artery/vein determination on the blood vessel in the blood vessel single-body region based on a result of artery/vein determination on each of the blood vessels in the blood vessel aggregate region.

5. The information processing apparatus according to claim 4, in which the processor is configured to compare reliability of artery/vein determination on the blood vessel in the blood vessel single-body region with reliability of artery/vein determination on each of the blood vessels in the blood vessel aggregate region, and select a determination result having higher reliability.

6. The information processing apparatus according to claim 5, in which the processor is configured to display each of the blood vessels included in the blood vessel aggregate region such that an artery and a vein can be identified from each other based on a correction result.

7. The information processing apparatus according to claim 6, in which the processor is configured to display, on the display device, reliability on the selected determination result.

8. The information processing apparatus according to claim 7, in which the processor is configured to display, on the display device, a message urging an operator to pay attention in a case where the reliability on the selected determination result is lower than a certain value.

9. The information processing apparatus according to claim 1, in which the processor is configured to highlight the blood vessel aggregate region by surrounding the blood vessel aggregate with a single frame in the ultrasound image.

10. The information processing apparatus according to claim 9, wherein the displacement amount is a distance of each of the blood vessels from the center of the single frame in the ultrasound image.

11. An information processing method for performing processing of causing a display device to display an ultrasound image, which is generated by transmitting ultrasound beams from a transducer array toward the inside of a living body and receiving ultrasound echoes generated in the living body, the method comprising:

detecting, from the ultrasound image, a blood vessel aggregate region including a blood vessel aggregate in which three or more blood vessels are aggregated, the blood vessel aggregate comprising at least one artery and at least one vein, wherein the blood vessel aggregate region is a limited region within the ultrasound image, highlighting and displaying the detected blood vessel aggregate region in the ultrasound image, calculating a displacement amount of each of the blood vessels from a center of the blood vessel aggregate region, and determining whether each of the blood vessels is an artery or a vein based on the calculation.

12. A non-transitory computer-readable storage medium storing a program causing a computer to execute a process of causing a display device to display an ultrasound image, which is generated by transmitting ultrasound beams from a transducer array toward the inside of a living body and receiving ultrasound echoes generated in the living body, the process comprising:

detecting, from the ultrasound image, a blood vessel aggregate region including a blood vessel aggregate in which three or more blood vessels are aggregated, the blood vessel aggregate comprising at least one artery and at least one vein, wherein the blood vessel aggregate region is a limited region within the ultrasound image, highlighting and displaying the detected blood vessel aggregate region in the ultrasound image, calculating a displacement amount of each of the blood vessels from a center of the blood vessel aggregate region, and determining whether each of the blood vessels is an artery or a vein based on the calculation.

* * * * *